US011963772B2

(12) United States Patent
Suzuki et al.

(10) Patent No.: US 11,963,772 B2
(45) Date of Patent: Apr. 23, 2024

(54) SYSTEM, COMPUTER-READABLE NON-TRANSITORY RECORDING MEDIUM, AND METHOD FOR ESTIMATING PSYCHOLOGICAL STATE OF USER

(71) Applicant: Panasonic Intellectual Property Management Co., Ltd., Osaka (JP)

(72) Inventors: Masato Suzuki, Kyoto (JP); Takamasa Ando, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 18/064,621

(22) Filed: Dec. 12, 2022

(65) Prior Publication Data

US 2023/0111721 A1 Apr. 13, 2023

Related U.S. Application Data

(63) Continuation of application No. 16/985,261, filed on Aug. 5, 2020, now Pat. No. 11,557,148, which is a
(Continued)

(30) Foreign Application Priority Data

Mar. 15, 2018 (JP) .................. 2018-047811

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0064* (2013.01); *G06F 18/24* (2023.01); *G06V 10/145* (2022.01); *G06V 40/174* (2022.01)

(58) Field of Classification Search
CPC ................... A61B 5/165; A61B 5/0064; A61B 2562/0233; A61B 5/0022; A61B 5/0261;
(Continued)

(56) References Cited

U.S. PATENT DOCUMENTS 5,305,759 A 4/1994 Kaneko et al.
5,994,857 A * 11/1999 Peterson, Jr. .......... B60K 28/04
307/9.1
(Continued)

FOREIGN PATENT DOCUMENTS

EP 3175786 A1 6/2017
JP 4-189349 7/1992
(Continued)

OTHER PUBLICATIONS

International Search Report of PCT application No. PCT/JP2019/007430 dated May 21, 2019.
(Continued)

*Primary Examiner* — Wesley J Tucker
(74) *Attorney, Agent, or Firm* — Rimon P.C.

(57) ABSTRACT

A system includes: a light source that emits pulsed light that illuminates a user's head portion; a photodetector that detects at least part of pulsed light returning from the head portion and that outputs one or more signals corresponding to an intensity of the at least part; electrical circuitry; and a memory that stores an emotion model indicating a relationship between the one or more signals and emotions. Based on a change in the one or more signals, the electrical circuitry selects an emotion by referring to the model. The one or more signals include a first signal corresponding to an intensity of first part of the reflection pulsed light and a second signal corresponding to an intensity of second part of the reflection pulsed light. The first part incudes part before
(Continued)

a falling period is started; and the second part includes at least part in the falling period.

9 Claims, 18 Drawing Sheets

Related U.S. Application Data continuation of application No. PCT/JP2019/007430, filed on Feb. 27, 2019.

(51) Int. Cl.
  *G06F 18/24* (2023.01)
  *G06V 10/145* (2022.01)
  *G06V 40/16* (2022.01)

(58) Field of Classification Search
  CPC ... A61B 5/6803; A61B 5/6891; A61B 5/6893; A61B 5/6898; A61B 5/7475; G06F 18/24; G06V 10/145; G06V 40/174; Y02B 20/40; H05B 47/105
  See application file for complete search history.

(56) References Cited

U.S. PATENT DOCUMENTS

| | | | |
|---|---|---|---|
| 5,995,857 A * | 11/1999 | Toomim | A61B 5/6814 |
| | | | 600/340 |
| 7,388,971 B2 | 6/2008 | Rice et al. | |
| 9,531,708 B2 | 12/2016 | Cornell et al. | |
| 2004/0106856 A1* | 6/2004 | Kimura | A61B 5/0062 |
| | | | 250/341.1 |
| 2005/0075532 A1 | 4/2005 | Lee et al. | |
| 2008/0214903 A1 | 9/2008 | Orbach | |
| 2009/0318773 A1* | 12/2009 | Jung | A61B 5/4803 |
| | | | 600/300 |
| 2012/0130203 A1 | 5/2012 | Stergiou et al. | |
| 2014/0267090 A1* | 9/2014 | Heyman | G06F 3/0481 |
| | | | 345/173 |
| 2015/0099987 A1 | 4/2015 | Bhatkar et al. | |
| 2015/0173618 A1* | 6/2015 | Kusukame | A61B 5/4064 |
| | | | 600/473 |
| 2015/0254955 A1 | 9/2015 | Fields et al. | |
| 2015/0350201 A1 | 12/2015 | Cornell et al. | |
| 2017/0112381 A1 | 4/2017 | Kumar et al. | |
| 2017/0150930 A1 | 6/2017 | Shikii et al. | |
| 2017/0345424 A1 | 11/2017 | Ikeno et al. | |
| 2017/0353672 A1* | 12/2017 | Nakamura | A61B 5/7207 |
| 2018/0176496 A1 | 6/2018 | Nakamura et al. | |
| 2018/0314879 A1 | 11/2018 | Khwaja et al. | |
| 2019/0014994 A1* | 1/2019 | Shiono | A61B 5/0261 |
| 2019/0017932 A1* | 1/2019 | Shiono | G01N 21/474 |
| 2019/0028660 A1* | 1/2019 | Ando | H04N 23/11 |
| 2019/0100175 A1* | 4/2019 | Takeuchi | G08G 1/166 |
| 2019/0239792 A1 | 8/2019 | Mukai et al. | |
| 2019/0339772 A1* | 11/2019 | Yoshida | G06F 3/013 |
| 2020/0107730 A1* | 4/2020 | Yanagida | G06V 40/176 |
| 2020/0297270 A1* | 9/2020 | Ando | A61B 5/0073 |
| 2020/0364445 A1* | 11/2020 | Suzuki | A61B 5/0064 |
| 2021/0064855 A1 | 3/2021 | Wang et al. | |
| 2021/0085229 A1* | 3/2021 | Narumi | A61B 5/0261 |
| 2021/0236006 A1* | 8/2021 | Nakamura | A61B 5/165 |
| 2021/0393206 A1* | 12/2021 | Kusanagi | G06F 3/14 |
| 2022/0378298 A1* | 12/2022 | Yanagida | A61B 10/00 |
| 2022/0400964 A1* | 12/2022 | Imai | A61B 10/00 |
| 2023/0083178 A1* | 3/2023 | Ando | G01N 21/49 |
| | | | 356/4.01 |

FOREIGN PATENT DOCUMENTS

| | | |
|---|---|---|
| JP | 11-164826 | 6/1999 |
| JP | 2004-024879 | 1/2004 |
| JP | 2008-532587 | 8/2008 |
| JP | 2009-042671 | 2/2009 |
| JP | 2012-110715 | 6/2012 |
| JP | 2017-068810 A | 4/2017 |
| JP | 2017-099846 A | 6/2017 |
| JP | 2017-100039 | 6/2017 |
| JP | 2017-124153 | 7/2017 |
| JP | 2017-215468 | 12/2017 |
| JP | 2017-220926 | 12/2017 |
| JP | 2018-005596 | 1/2018 |
| JP | 2018-096988 | 6/2018 |

OTHER PUBLICATIONS

Naoyuki Hayashi, "32. Human emotional sensing using non-contact measurement of facial skin blood flow", The Jehara Memorial Foundation Research Report Collection, vol. 26, 2012, pp. 1-4.

Masato Fukuda, "Optical Topography as an Auxiliary Laboratory Test for Differential Diagnosis of Depressive State : Clinical Application of Near-infrared Spectroscopy (NIRS) as the First Trial for Approved Laboratory Tests in Psychiatry", Psychiatry and Clinical Neurosciences, 117 (2), 2015, pp. 79-93.

Peter D. Drummond et al., "The effect of expressing anger on cardiovascular reactivity and facial blood flow in Chinese and Caucasians", Psychophysiology, 38, Mar. 2001, pp. 190-196.

Communication pursuant to Rule 164(1) EPC dated Feb. 18, 2021 for the related European Patent Application No. 19767745.3.

Park Min Woo et al: "Individual Emotion Classification between Happiness and Sadness by Analyzing Photoplethysmography and Skin Temperature", 2013 Fourth World Congress on Software Engineering, IEEE, Dec. 3, 2013 (Dec. 3, 2013), pp. 190-194, XP032580458.

Non-Final Office Action dated Jun. 7, 2022 issued in U.S. Appl. No. 16/985,261.

Notice of Allowance dated Sep. 21, 2022 issued in U.S. Appl. No. 16/985,261.

English Translation of Chinese Search Report dated Nov. 30, 2023 for the related Chinese Patent Application No. 201980009787.9.

* cited by examiner

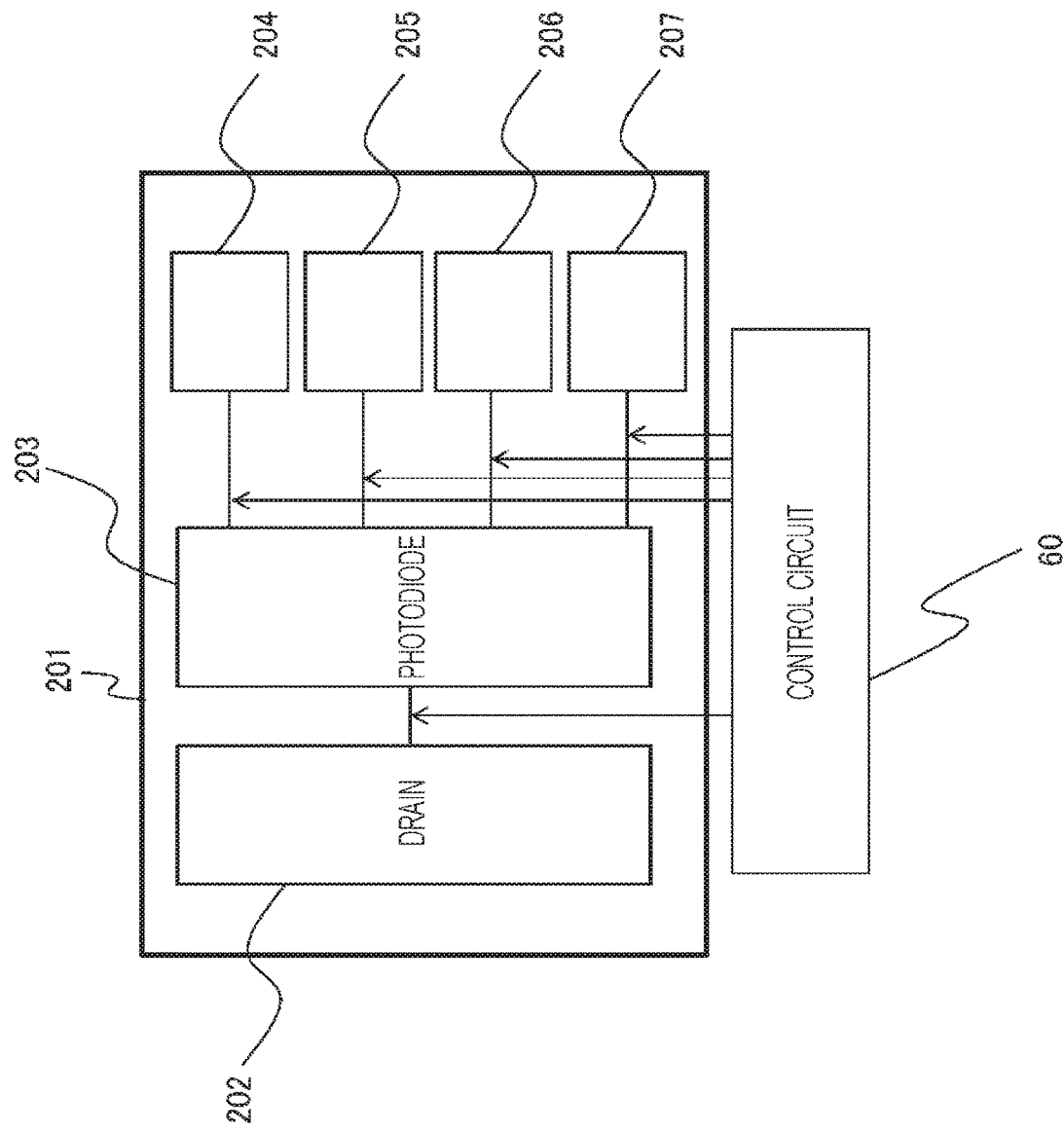

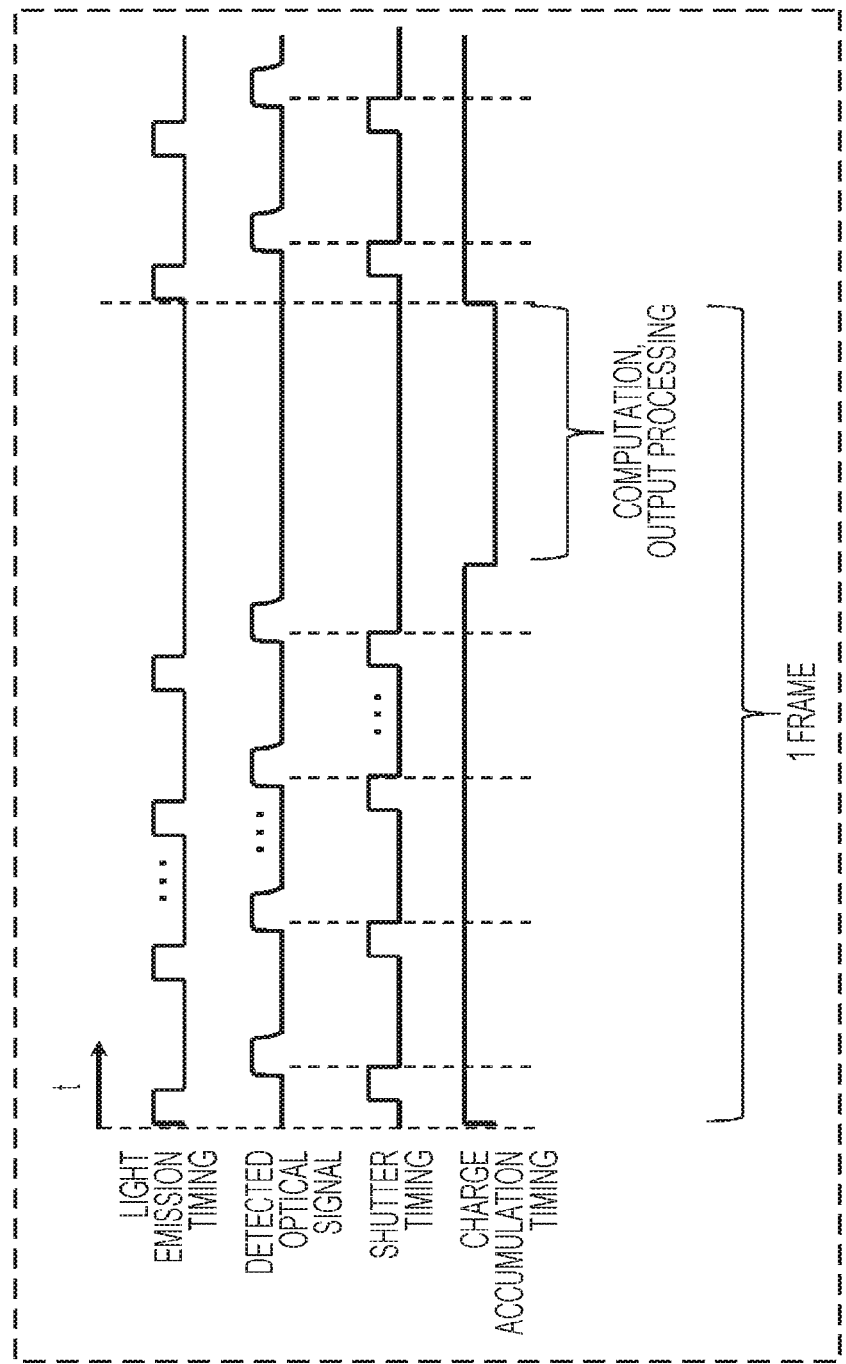

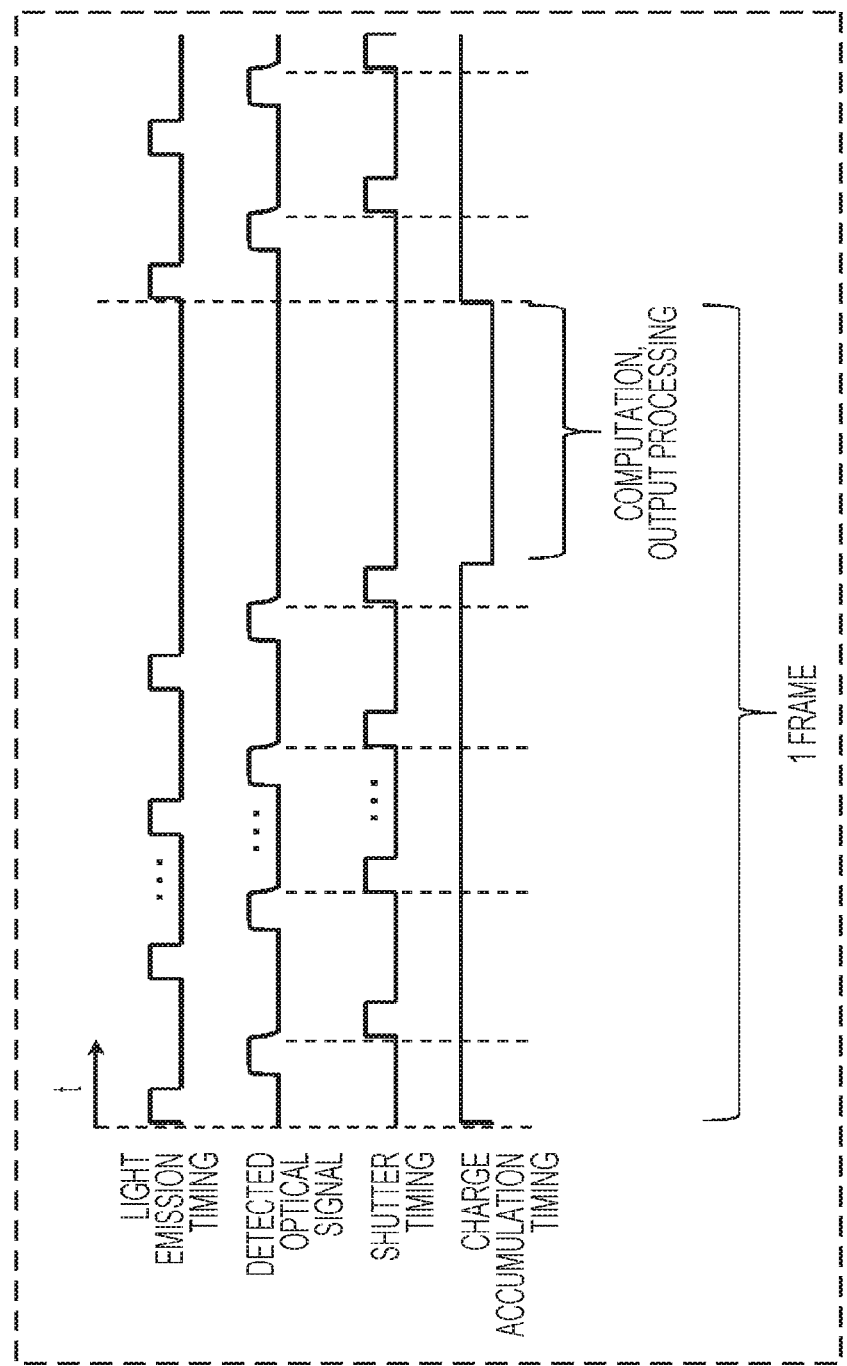

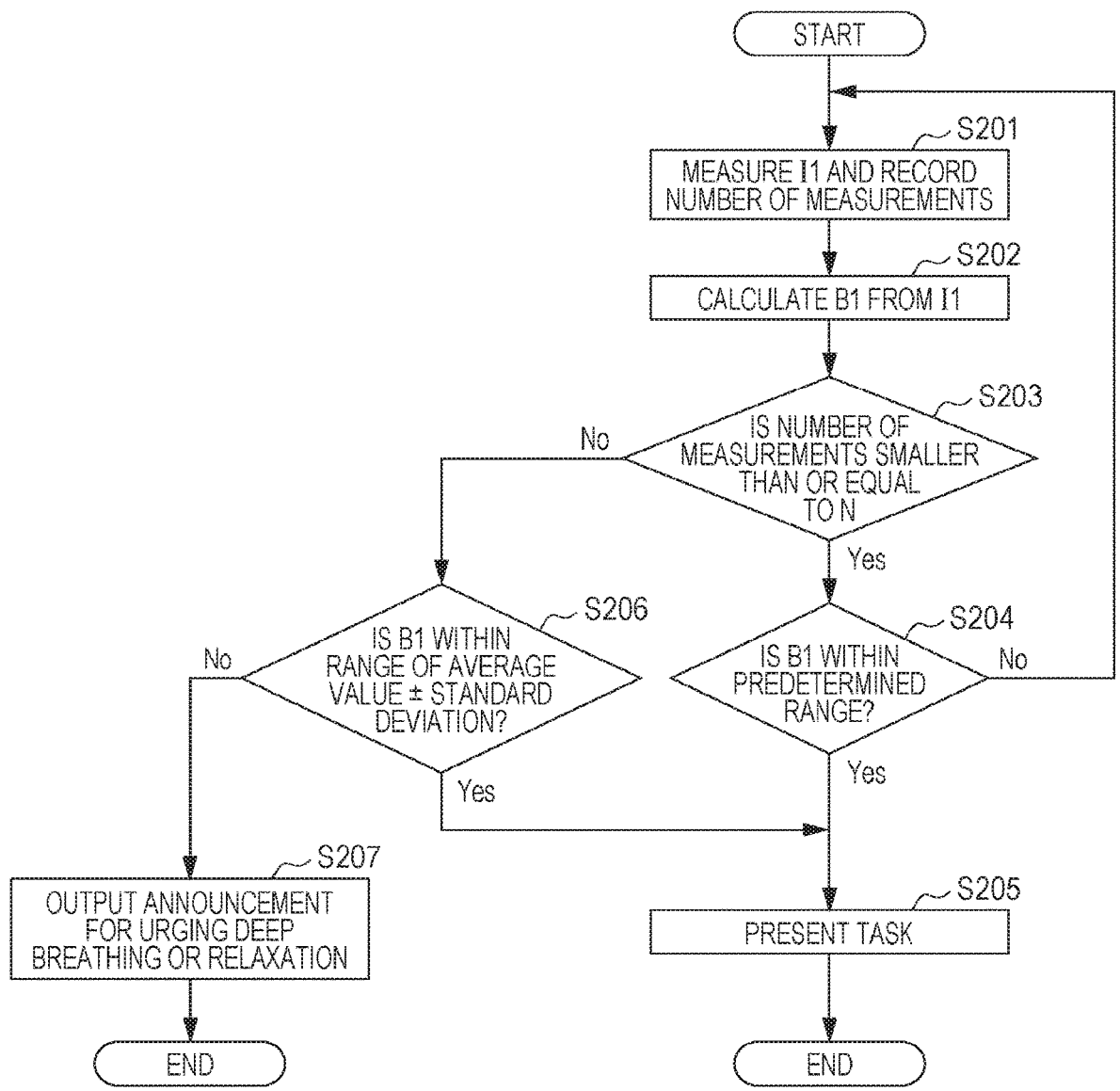

SYSTEM, COMPUTER-READABLE NON-TRANSITORY RECORDING MEDIUM, AND METHOD FOR ESTIMATING PSYCHOLOGICAL STATE OF USER

CROSS-REFERENCE TO RELATED APPLICATIONS

This application is a Continuation of U.S. patent application Ser. No. 16/985,261, filed on Aug. 5, 2020, which is a Continuation of International Patent Application No. PCT/JP2019/007430, filed on Feb. 27, 2019, which claims the benefit of foreign priority of Japanese Patent Application No. 2018-047811, filed on Mar. 15, 2018, the contents all of which are incorporated herein by reference.

BACKGROUND

1. Technical Field

The present disclosure relates to a system, a computer-readable non-transitory recording medium, and a method for estimating a psychological state of a user.

2. Description of the Related Art

It has been known that the skin blood flow and the cerebral blood flow change due to changes in the emotion of the human. Also, 32. Human Affect Sensing Utilizing Contactless Measurement of Facial Skin Blood Flow "Research Reports of Uehara Memorial Life Science Foundation, 26 (2012)", which is hereinafter referred to as "Non-Patent Document 1", discloses that the pattern of the facial blood flow changes according to the emotion of a target person. The pattern of the facial blood flow can be obtained by imaging an entire-facial blood flow distribution using a laser-speckle blood flowmeter. "Optical Topography as an Auxiliary Laboratory Test for Differential Diagnosis of Depressive State" Psychiatria et Neurologia Japonica, Vol. 117, No. 2, pp. 79-93 (2015), which is hereinafter referred to as "Non-Patent Document 2", discloses a method in which near-infrared spectroscopy is used to determine a major depressive disorder from the state of cerebral blood flow including blood flow in the scalp in the forehead portion.

SUMMARY

In one general aspect, the techniques disclosed here feature a system including: a light source that emits pulsed light with which a head portion of a user is illuminated; a photodetector that detects at least part of reflection pulsed light that returns from the head portion and that outputs one or more signals corresponding to an intensity of the at least part of the reflection pulsed light; electrical circuitry that controls the light source and the photodetector to process the one or more signals output from the photodetector; and a first memory that stores an emotion model indicating a relationship between the one or more signals and emotions. Based on a change in the one or more signals, the electrical circuitry selects at least one emotion from among the emotions by referring to the emotion mode. The one or more signals include a first signal corresponding to an intensity of first part of the reflection pulsed light and a second signal corresponding to an intensity of second part of the reflection pulsed light, the second part being different from the first part. The first part incudes part before a falling period is started, the falling period being a period from start to end of a decrease of an intensity of the reflection pulsed light; and the second part includes at least part in the falling period.

It should be noted that general or specific embodiments may be implemented as a system, an apparatus, a device, a method, an integrated circuit, a computer program, a recording medium, or any selective combination thereof. The general or specific embodiments may be implemented as any selective combination of a system, an apparatus, a device, a method, an integrated circuit, a computer program, and a recording medium.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1D is a diagram illustrating an example of a schematic configuration of one pixel in the photodetector;

FIG. 3A is a diagram illustrating one example of a timing chart for detection of surface reflection components;

FIG. 3B is a diagram illustrating one example of a timing chart for detection of the internal scattering components;

FIG. 4 is a flowchart illustrating one example of processing for estimating the state of a user before measurement;

DETAILED DESCRIPTION

Figure 1A:
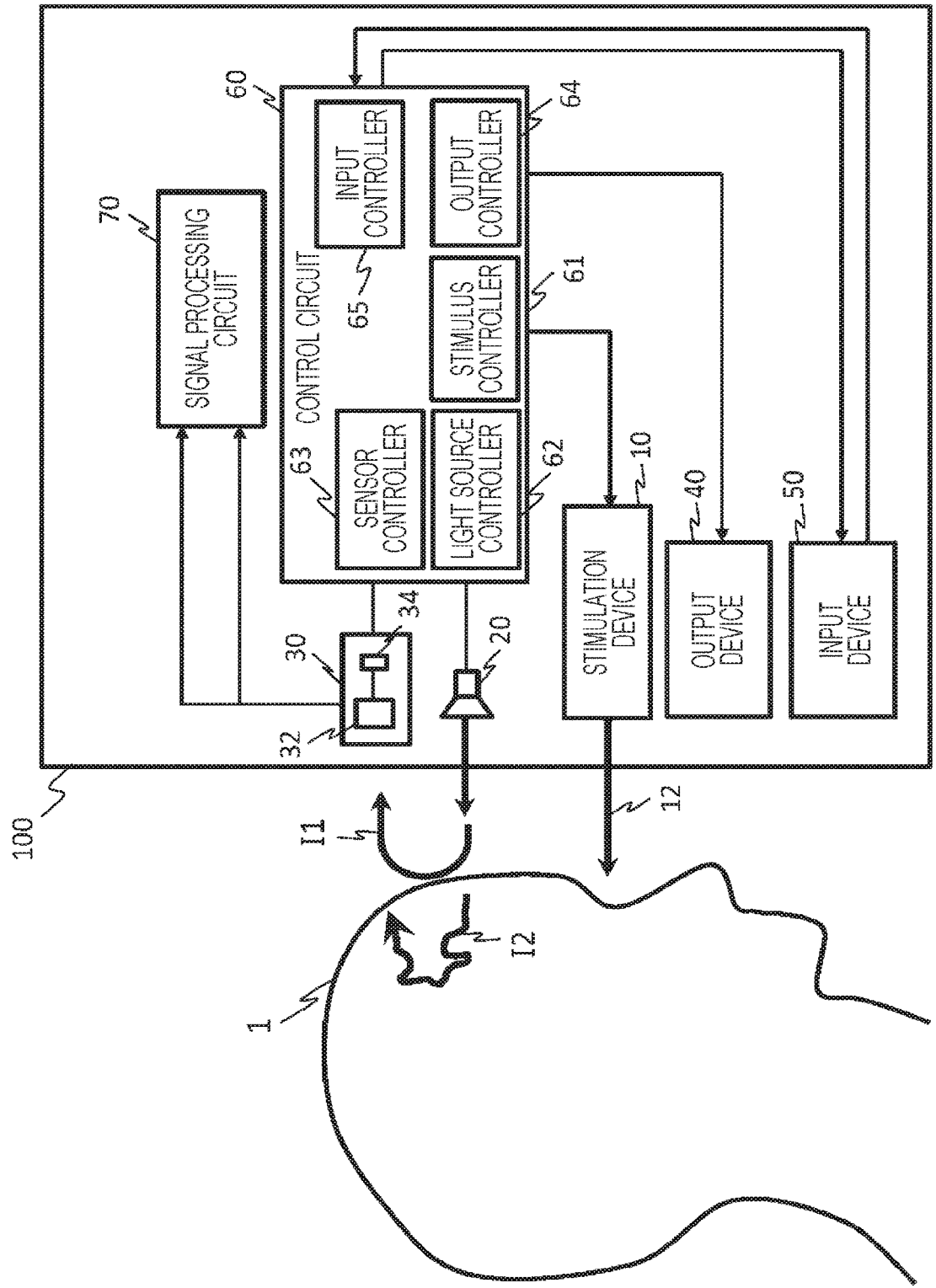
FIG. 1A is a schematic diagram illustrating a system according to an embodiment of the present disclosure.

The embodiments described below each represent a general or specific example. Numerical values, shapes, materials, constituent elements, the arrangement positions of constituent elements, and so on described in the embodiments below are examples and are not intended to limit the technology of the present disclosure. Also, of the constituent elements in the embodiments described below, the constituent elements not set forth in the independent claims that represent the broadest concept will be described as optional constituent elements.

In the present disclosure, all or a part of any of circuits, units, devices, parts, portions, or any of functional blocks in the block diagrams may be implemented as one or more of electronic circuits including, but not limited to, a semiconductor device, a semiconductor integrated circuit (IC) or a large-scale integration (LSI). The LSI or IC can be integrated into one chip, or also can be a combination of plural chips. For example, functional blocks other than a memory may be integrated into one chip. The name used here is LSI or IC, but it may also be called system LSI, very large-scale integration (VLSI), or ultra large-scale integration (ULSI) depending on the degree of integration. A field programmable gate array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a read-only memory (ROM), an optical disk or a hard disk drive, and when the software is executed by a processor, the software causes the processor together with peripheral devices to execute the functions specified in the software. A system, apparatus, or device may include such one or more non-transitory recording media on which the software is recorded and a processor together with necessary hardware devices such as an interface.

Embodiments will be described below in detail with reference to the accompanying drawings. In the following description, the same or similar constituent elements are denoted by the same reference numerals.

Embodiment

1. System

The configuration of a living-body measurement system 100 according to an exemplary embodiment of the present disclosure will be described with reference to FIGS. 1A to 3B.

FIG. 1A is a schematic diagram illustrating the living-body measurement system 100 according to the present embodiment. The living-body measurement system 100 includes a stimulation device 10, a light source 20, a photodetector 30, an output device 40, an input device 50, a control circuit 60, and a signal processing circuit 70. The control circuit 60 and the signal processing circuit 70 are one example of electrical circuitry in the present disclosure.

The stimulation device 10 provides a stimulus to a user 1. The light source 20 emits pulsed light with which the head portion of the user 1 is illuminated. The photodetector 30 detects at least part of pulsed light that returns from the head portion of the user 1. The output device 40 outputs, to the user 1, a result based on processing in the signal processing circuit 70. The input device 50 receives an input of the user 1. The control circuit 60 controls the stimulation device 10, the light source 20, the photodetector 30, the output device 40, and the input device 50. The signal processing circuit 70 processes signals output from the photodetector 30.

In the present embodiment, the control circuit 60 includes a stimulus controller 61 that controls the stimulation device 10, a light source controller 62 that controls the light source 20, a sensor controller 63 that controls the photodetector 30, an output controller 64 that controls the output device 40, and an input controller 65 that controls the input device 50. The stimulus controller 61 controls at least one of the hue, chroma, and brightness of video provided as a stimulus 12 or at least one of the sound quality and volume of sound. The light source controller 62 controls the intensity, the pulse duration, the emission timing, and/or the wavelength of the pulsed light emitted from the light source 20. The sensor controller 63 controls timing of signal accumulation in each pixel in the photodetector 30. The output controller 64 controls at least one of the hue, chroma, and brightness of video that is output or at least one of the sound quality and volume of sound that is output. The input controller 65 controls the start and the end of input reception.

Herein, the "biological reaction" means a change in the living-body information of the user 1 when the stimulus 12 is provided. The "living-body information" refers to a measurable quantity of a living body that changes in response to the stimulus 12. The living-body information includes, for example, various quantities, such as a blood flow rate, a blood pressure, a heart rate, a pulse rate, a respiration rate, a body temperature, a brain wave, the concentration of oxygenated hemoglobin in blood, the concentration of deoxygenated hemoglobin in blood, the saturation level of oxygen in blood, and reflection spectra of skin. Some of the living-body information may be called vital signs. The constituent elements of the living-body measurement system 100 will be described below.

1-1. Stimulation Device

The stimulation device 10 provides the stimulus 12 to the user 1. The stimulus 12 causes biological reaction of the user 1. The stimulation device 10 can include, for example, at least one of a display and a speaker. The stimulation device 10 provides, for example, at least one stimulus 12 of video and sound to the user 1. The video is a stimulus to the visual sense, and the sound is a stimulus to the auditory sense. FIG. 1A schematically illustrates a situation in which the stimulation device 10 that includes a display provides video to the user 1 as the stimulus 12. This visual stimulus may be, for example, any type of task, such as a calculation question, a language question, a puzzle, a quiz, or a game. Simultaneously with presenting the task, the stimulation device 10 may output sound corresponding to the task. Other than video or sound content, the visual stimulus may be a change in the brightness or the color of lighting in a room.

Other than the stimulus 12 to the visual sense or the auditory sense, a stimulus 12 to a tactile sensation, olfaction, or gustation may be provided. The stimulation device 10 has a structure and a function that differ depending on the types of stimulus given to the user 1. For example, when a tactile stimulus is to be given to the user 1, the stimulation device 10 may be a device that generates vibration or heat. When an olfactory stimulus is to be given to the user 1, the stimulation device 10 may be a device that generates odor.

1-2. Light Source

The light source 20 illuminates the head portion (for example, the forehead) of the user 1 with light. Light that is emitted from the light source 20 and that reaches the user 1 splits into surface reflection components I1 that are reflected by a surface of the user 1 and internal scattering components I2 that scatter inside the user 1. The internal scattering components I2 are components that reflect or scatter once or that scatter one or more times inside the living body. When the forehead of the user 1 is illuminated with light, the internal scattering components I2 refer to components that reach a portion, for example, the brain, at a depth of about 8 to 16 mm from the surface of the forehead and that return to the living-body measurement system 100 again. The surface reflection components I1 include three components: a direct reflection component, a diffusion reflection component, and a scattering reflection component. The direct reflection component is a reflection component whose incident angle and reflection angle are equal to each other. The diffusion reflection component is a component that diffuses and reflects on an uneven shape on a surface. The scattering reflection component is a component that scatters and reflects in internal tissue in the vicinity of a surface. When the forehead of the user 1 is illuminated with light, the scattering reflection component is a component that scatters and reflects inside the epidermis. Hereinafter, in the present disclosure, the surface reflection components I1 that reflect on the surface of the user 1 are assumed to include those three components. The surface reflection components I1 and the internal scattering components I2 change in traveling direction owing to reflection or diffusion, and some of the surface reflection components I1 and the internal scattering components I2 reach the photodetector 30.

First, a description will be given of a method for obtaining the internal scattering components I2. In accordance with an instruction from the control circuit 60, the light source 20 repeatedly generates pulsed light a plurality of times at predetermined time intervals or at a predetermined timing. The pulsed light generated by the light source 20 can have, for example, a rectangular wave whose falling period is nearly zero. Herein, the "falling period" is a period from when the intensity of pulsed light starts decreasing until the decrease ends. In general, light that is incident on the user 1 propagates in the user 1 through various paths and is emitted from the surface of the user 1 with time differences. Thus, the rear end of the internal scattering components I2 of the pulsed light has a spread. When the target portion is the forehead, the spread of the rear end of the internal scattering components I2 is about 4 ns. When this is considered, the falling period of the pulsed light can be set to, for example, 2 ns or less, which is half or less of the spread. The falling period may be 1 ns or less, which is further half of that falling period. The rising period of the pulsed light generated by the light source 20 is arbitrary. Herein, the "rising period" is a period from when the intensity of the pulsed light starts increasing until the increase ends. This is because, for detection of the internal scattering components I2 in the present embodiment, a falling portion of the pulsed light is used, and a rising portion of the pulse light is not used. The rising portion of the pulsed light can be used to detect the surface reflection components I1. The light source 20 can be, for example, a laser, such as a laser diode (LD), whose falling portion of the pulsed light is nearly orthogonal to the time axis, that is, whose time response characteristic is steep.

The wavelength of the light emitted by the light source 20 can be an arbitrary wavelength included in a wavelength range of, for example, 650 to 950 nm. This wavelength range is included in the wavelength range of red to near-infrared. Herein, terms for "light" are used not only for visible light but also for infrared. The aforementioned wavelength range is called the "biological window" and has a characteristic of being relatively less likely to absorbed by the in-vivo water and the skin. When a living body is the detection target, use of light in the above-described wavelength range can increase the detection sensitivity. As in the present embodiment, for detecting changes in blood flow in the skin and the brain of the user 1, light that is used is thought to be mainly absorbed by oxygenated hemoglobin ($HbO_2$) and deoxygenated hemoglobin (Hb). The oxygenated hemoglobin and the deoxygenated hemoglobin differ from each other in wavelength dependence of light absorption. In general, when changes occur in the blood flow, the concentrations of the oxygenated hemoglobin and the deoxygenated hemoglobin change, so that the degree of light absorption also changes. Accordingly, when the blood flow changes, the amount of light that is detected also changes over time.

The light source 20 may emit light having two or more wavelengths included in the aforementioned wavelength range. Such light having a plurality of wavelengths may be emitted from respective light sources.

In the living-body measurement system 100 in the present embodiment, the light source 20 that is designed considering influences on the retina can be used in order to perform measurement on the user 1 in a contactless manner. For example, the light source 20 that satisfies class 1 of a laser safety standard formulated in each country can be used. When class 1 is satisfied, the user 1 is illuminated with low-illuminance light with which the accessible emission level (AEL) falls below 1 mW. The light source 20 itself does not necessarily have to satisfy class 1. For example, a diffuser plate, a neutral density (ND) filter, or the like may be disposed in front of the light source 20 to diffuse or attenuate light to thereby satisfy class 1 of the laser safety standard.

Heretofore, streak cameras have been used in order to perform detection through discrimination of information, such as absorption coefficients or diffusion coefficients, at different positions in a depth direction inside the living body. For example, Japanese Unexamined Patent Application Publication No. 4-189349 discloses one example of such streak cameras. In these streak cameras, ultrashort pulsed light having a pulse duration of femtoseconds or picoseconds has been used in order to perform measurement with desired spatial resolutions.

In contrast, the living-body measurement system 100 in the present disclosure can discriminate and detect the surface reflection components I1 and the internal scattering components I2. Accordingly, the pulsed light emitted by the light source 20 does not necessarily have to be ultrashort pulsed light, and the pulse duration can be selected arbitrarily.

For illuminating the forehead with light in order to measure cerebral blood flow, the amount of light of the internal scattering components I2 can have a very small value, which is about one several-thousandths to one several-tenths of thousands of the amount of light of the surface reflection components I1. In addition, when the safety standards of the laser are considered, the amount of light that can be emitted is significantly small, thus making it very difficult to detect the internal scattering components I2. Even in this case, when the light source 20 generates pulsed light having a relatively long pulse duration, it is possible to increase the amount of summation of the internal scattering components I2 which involves a time delay. This can increase the amount of light that is detected and can enhance the signal/noise (S/N) ratio.

Figure 1B:
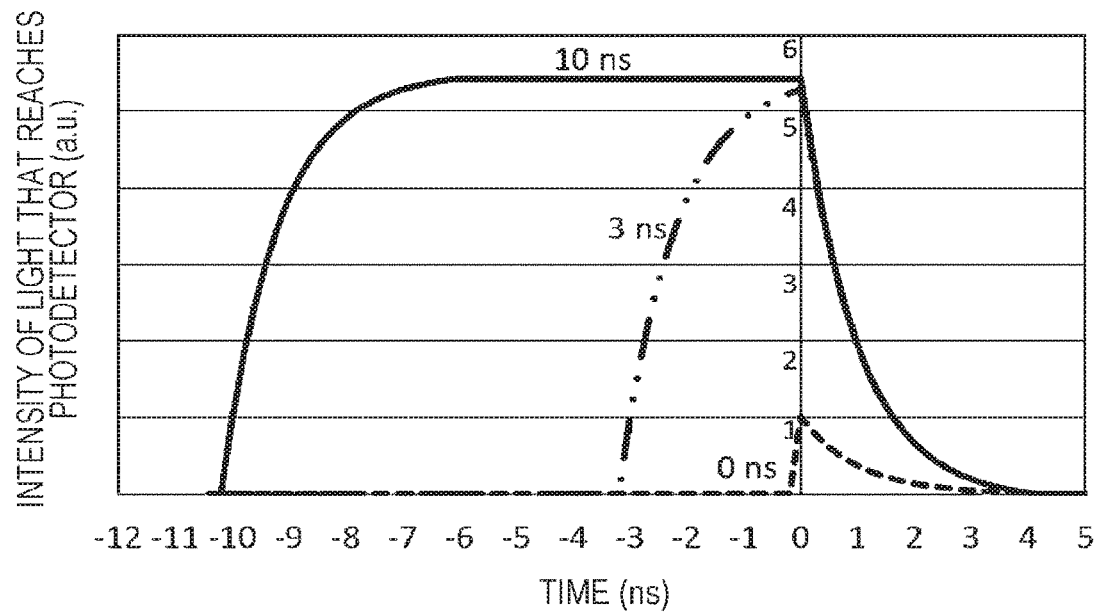
FIG. 1B is a graph illustrating an example of changes over time in the intensity of light that reaches a photodetector.
Figure 1C:
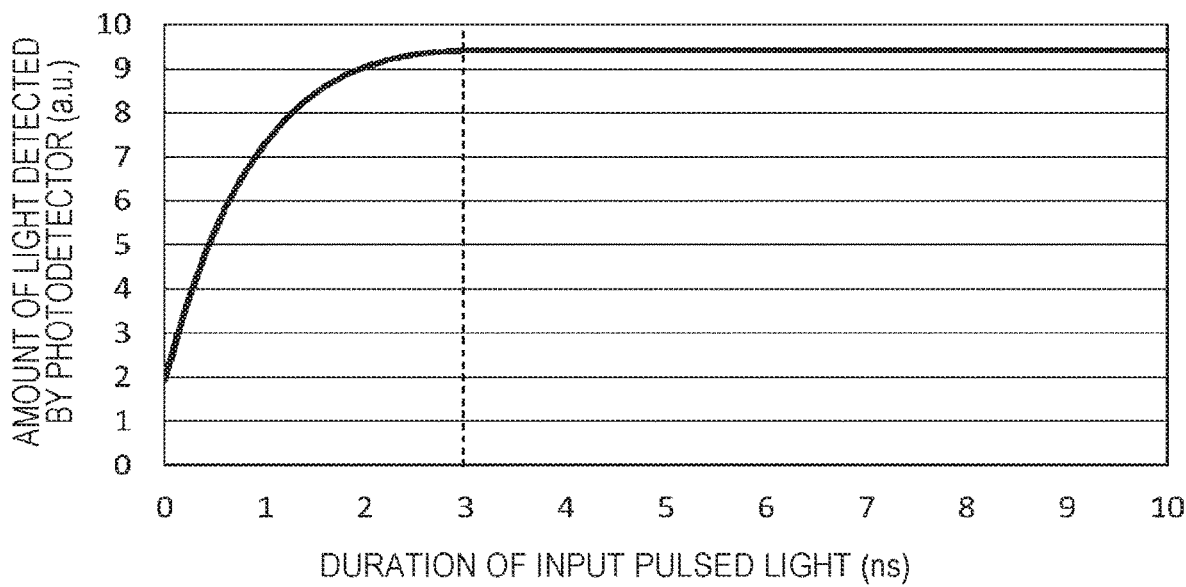
FIG. 1C is a graph in which the horizontal axis represents the duration of input pulsed light, and the vertical axis represents the amount of light detected by a photodetector.

The light source 20 emits, for example, pulsed light having a pulse duration of 3 ns or more. In general, the temporal spread of light that is scattered in physiological tissues, such as the brain, is about 4 ns. FIG. 1B illustrates an example of changes over time in the amount of light that reaches the photodetector 30 in respective cases in which the durations of input pulsed light are 0 ns, 3 ns, and 10 ns. As illustrated in FIG. 1B, as the duration of the pulsed light from the light source 20 is increased, the amount of light of the internal scattering components I2 that appear at the rear-end portion of pulsed light that returns from the user 1 increases. FIG. 1C is a graph in which the horizontal axis represents the duration of input pulsed light, and the vertical axis represents the amount of light detected by the photodetector 30. The photodetector 30 has an electronic shutter. The result in FIG. 1C was obtained under a condition that the electronic shutter was opened when 1 ns passed after the time point at which the rear end of the pulsed light reflected by the surface of the user 1 reached the photodetector 30. The reason why this condition was selected is that immediately after the rear end of the pulsed light reaches the photodetector 30, the ratio of the surface reflection components I1 to the internal scattering components I2 is high. As illustrated in FIG. 1C, when the pulse duration of pulsed light emitted by the light source 20 was set to 3 ns or more, it is possible to maximize the amount of light detected by the photodetector 30.

The light source 20 may emit pulsed light having a pulse duration of 5 ns or more or further 10 ns or more. On the other hand, when the pulse duration is too large, the amount of light that is not used increases and is thus wasteful. Hence, the light source 20 generates, for example, pulsed light having a pulse duration or 50 ns less. Alternatively, the light source 20 may emit pulsed light having a pulse duration of 30 ns less or further 20 ns or less.

The illumination pattern of the light source 20 may be, for example, a pattern having a uniform intensity distribution in an illumination area. In this respect, the present embodiment differs from a living-body measurement device of related art disclosed in, for example, Japanese Unexamined Patent Application Publication No. 11-164826 and so on. In the device disclosed in Japanese Unexamined Patent Application Publication No. 11-164826, a detector and a light source are separated about 3 cm from each other to spatially separate surface reflection components from internal scattering components. Thus, discrete light illumination has to be performed. In contrast, the living-body measurement system 100 in the present embodiment can reduce the surface reflection components I1 by temporally separating the surface reflection components I1 from the internal scattering components I2. Thus, the light source 20 may be implemented by a light source with an illumination pattern having a uniform intensity distribution. A diffuser plate may diffuse light, emitted by the light source 20, to form an illumination pattern having a uniform intensity distribution.

In the present embodiment, the internal scattering components I2 can also be detected at a position immediately below an illumination point of the user 1, unlike the related art. It is also possible to enhance the measurement resolution by illuminating a spatially large range of the user 1 with light.

1-3. Photodetector

The photodetector 30 detects at least part of reflection pulsed light that returns from the head portion of the user 1. The photodetector 30 outputs one or more signals corresponding to the intensity of the detected light. The one or more signals include a signal corresponding to an intensity of at least part of the reflection pulsed light in the rising period and a signal corresponding to an intensity of at least part of the reflection pulsed light in the falling period.

The photodetector 30 includes a plurality of photoelectric conversion elements 32 and a plurality of charge accumulation portions 34. Specifically, the photodetector 30 has a plurality of two-dimensionally arranged light-detecting cells to obtain two-dimensional information of the user 1 at a time. Herein, the light-detecting cells may be referred to as "pixels". The photodetector 30 is, for example, an arbitrary image capture element, such as a CCD image sensor or a CMOS image sensor. More generally, the photodetector 30 includes at least one photoelectric conversion element 32 and at least one charge accumulation portion 34.

The photodetector 30 has an electronic shutter. The electronic shutter is a circuit for controlling an image capture timing. In the present embodiment, the sensor controller 63 in the control circuit 60 has functions of the electronic shutter. The electronic shutter controls a single-signal-accumulation period in which received light is converted into effective electrical signals and the electrical signals are stored and a period in which the signal accumulation is stopped. The signal accumulation period can also be referred to as an "exposure period" or a "photography period". The length of the exposure period may be referred to as a "shutter duration" in the description below. The time from when one exposure period ends until a next exposure period starts may be referred to as a "non-exposure period". Hereinafter, a state in which exposure is performed may be referred to as "open", and a state in which exposure is stopped may be referred to as "close".

The photodetector 30 can adjust the exposure period and the non-exposure period in the range of subnanoseconds, for example, in the range of 30 ps to 1 ns, by using the electronic shutter. In order to correct influences of the brightness of the subject, typical time-of-flight (ToF) cameras intended for distance measurement detect all light that is emitted from the light source 20 and returns through reflection by a subject. Accordingly, in the typical ToF cameras, the shutter duration needs to be larger than the pulse duration of light. In contrast, in the living-body measurement system 100 in the present embodiment, it is not necessary to correct the amount of light of a subject. Thus, the shutter duration does not need to be larger than the pulse duration. Hence, the shutter duration can be set to, for example, a value of 1 to 30 ns. According to the living-body measurement system 100 in the present embodiment, since the shutter duration can be reduced, it is possible to reduce influences of dark current included in detection signals.

For illuminating the forehead of the user 1 with light to detect information of cerebral blood flow or the like, the decay rate of light inside the forehead is very large. For example, the emitted light can decay to about one millionth of the incident light. Thus, there are cases in which the amount of light is not sufficient with only illumination of a single pulse in order to detect the internal scattering components I2. The amount of light is particularly very small with illumination at class 1 of the laser safety standard. In this case, the light source 20 emits the pulsed light a plurality of times, and correspondingly, the photodetector 30 also performs exposure a plurality of times by using an electronic shutter, to thereby make it possible to improve the sensitivity through summation of detection signals.

A configuration example of the photodetector 30 will be described below.

The photodetector 30 includes a plurality of pixels that is two-dimensionally arrayed on an image capture plane. Each pixel can include, for example, a photoelectric conversion element 32, such as a photodiode, and one or more charge accumulation portions 34. The description below will be given of an example in which each pixel includes a photoelectric conversion element 32 that performs photoelectric conversion to generate signal charge corresponding to the amount of received light, a charge accumulation portion 34 that accumulates signal charge generated from the surface reflection components I1 of the pulsed light, and a charge accumulation portion 34 that accumulates signal charge generated from the internal scattering components I2 of the pulsed light. In an example below, the control circuit 60 causes the photodetector 30 to detect pre-falling-start part of pulsed light that returns from the head portion of the user 1, to thereby detect the surface reflection components I1. The control circuit 60 also causes the photodetector 30 to detect post-falling-start part of the pulsed light that returns from the head portion of the user 1, to thereby detect the internal scattering components I2. The light source 20 is assumed to emit light with two types of wavelength.

FIG. 1D is a diagram illustrating a schematic configuration example of one pixel 201 in the photodetector 30. FIG. 1D schematically illustrates the configuration of one pixel 201 and does not necessarily reflect the actual structure thereof. The pixel 201 in this example includes a photodiode 203 that performs photoelectric conversion, first to fourth floating diffusion layers (floating diffusions) 204, 205, 206, and 207 that are charge accumulation portions, and a drain 202 that discharges signal charge.

The photodiode 203 converts photons that are incident on each pixel as a result of a single emission of pulsed light into signal electrons, which are signal charge. The converted signal electrons are discharged to the drain 202 in accordance with a control signal input from the control circuit 60 or are sorted to any of the first to fourth floating diffusion layers 204, 205, 206, and 207.

The emission of the pulsed light from the light source 20, the accumulation of the signal charges in the first floating diffusion layer 204, the second floating diffusion layer 205, the third floating diffusion layer 206, and the fourth floating diffusion layer 207, and the discharge of the signal charge to the drain 202 are repeatedly performed in that order. This repetition operation is performed at high speed and can be repeated, for example, tens of thousands of times to hundreds of millions of times within the time (for example, about 1/30 second) of one frame of a moving image. Eventually, the pixel 201 generates four image signals based on the signal charges accumulated in the first to fourth floating diffusion layers 204, 205, 206, and 207 and outputs the four image signals.

The control circuit 60 in this example causes the light source 20 to sequentially and repeatedly emit first pulsed light having a first wavelength and second pulsed light having a second wavelength. Selecting two wavelengths having different absorption rates for the internal tissues of the user 1 as the first wavelength and the second wavelength makes it possible to analyze the state of the user 1. For example, a wavelength that is larger than 805 nm may be selected as the first wavelength, and a wavelength that is smaller than 805 nm may be selected as the second wavelength. This makes it possible to detect respective changes in the concentration of oxygenated hemoglobin in blood of the user 1 and the concentration of deoxygenated hemoglobin therein.

The control circuit 60 first causes the light source 20 to emit the first pulsed light. In a first period in which the surface reflection components I1 of the first pulsed light are incident on the photodiode 203, the control circuit 60 causes signal charge to be accumulated in the first floating diffusion layer 204. Subsequently, in a second period in which the internal scattering components I2 of the first pulsed light are incident on the photodiode 203, the control circuit 60 causes signal charge be accumulated in the second floating diffusion layer 205. Next, the control circuit 60 causes the light source 20 to emit the second pulsed light. In a third period in which the surface reflection components I1 of the second pulsed light are incident on the photodiode 203, the control circuit 60 causes signal charge to be accumulated in the third floating diffusion layer 206. Subsequently, in a fourth period in which the internal scattering components I2 of the second pulsed light are incident on the photodiode 203, the control circuit 60 causes signal charge to be accumulated in the fourth floating diffusion layer 207.

As described above, after starting emission of the first pulsed light, the control circuit 60 causes signal charge from the photodiode 203 to be sequentially accumulated in the first floating diffusion layer 204 and the second floating diffusion layer 205 with a predetermined time difference therebetween. Thereafter, after starting emission of the second pulsed light, the control circuit 60 causes signal charge from the photodiode 203 to be sequentially accumulated in the third floating diffusion layer 206 and the fourth floating diffusion layer 207 with a predetermined time difference therebetween. The above-described operation is repeated a plurality of times. A period in which signal charge is accumulated in another floating diffusion layer (not illustrated) when the light source 20 is turned off may be provided in order to estimate the amount of light of external light and ambient light. By subtracting the amount of signal charge in the other floating diffusion layer mentioned above from the amount of signal charges in the first to fourth floating diffusion layers 204, 205, 206, and 207, it is possible to obtain signals from which components of the external light and the ambient light are eliminated.

Although the number of charge accumulation portions is four in the present embodiment, the number may be designed to a number that is two or more, depending on the purpose. For example, when only one type of wavelength is used, the number of charge accumulation portions may be two. Also, for an application in which the number of types of wavelength to be used is one, and the surface reflection components I1 are not detected, the number of charge accumulation portions per pixel may be one. Also, even for an application in which two or more types of wavelength are used, the number of charge accumulation portions may be one when image captures using the respective wavelengths are performed in different frames. Also, when the detection of the surface reflection components I1 and the detection of the internal scattering components I2 are performed in respective different frames, as described below, the number of charge accumulation portions may be one.

Figure 1E:
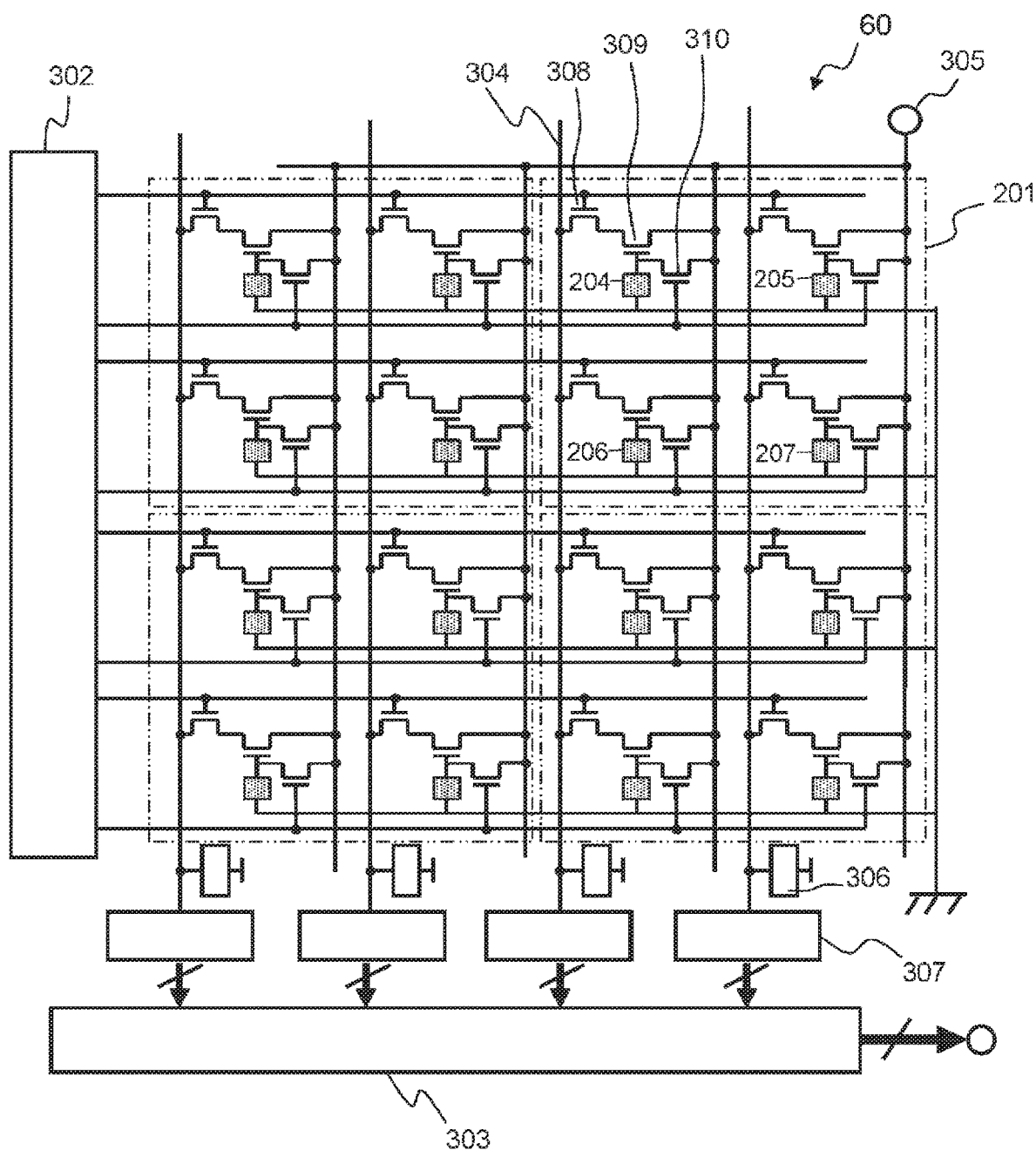
FIG. 1E is a diagram illustrating one example of the configuration of the photodetector.

FIG. 1E is a diagram illustrating one example of the configuration of the photodetector 30. In FIG. 1E, each area surrounded by a chain double-dashed line frame corresponds to one pixel 201. Each pixel 201 includes one photodiode. Although FIG. 1E illustrates only four pixels arrayed in two rows and two columns, a larger number of pixels can be arranged in practice. Each pixel 201 includes the first to fourth floating diffusion layers 204, 205, 206, and 207. The signals accumulated in the first to fourth floating diffusion layers 204, 205, 206, and 207 are treated as if they were signals of four pixels in a typical CMOS image sensor and are output from the photodetector 30.

Each pixel 201 has four signal detection circuits. Each signal detection circuit includes a source follower transistor 309, a row selecting transistor 308, and a reset transistor 310. In this example, the reset transistor 310 corresponds to the drain 202 illustrated in FIG. 1D, and a pulse that is input to a gate of the reset transistor 310 corresponds to a drain discharge pulse. Although each transistor is, for example, a field-effect transistor formed at a semiconductor substrate, the transistor is not limited thereto. As illustrated, one (typically, a source) of an input terminal and an output terminal of the source follower transistor 309, and one (typically, a drain) of an input terminal and an output terminal of the row selecting transistor 308 are connected to each other. A gate that is a control terminal of the source follower transistor 309 is connected to the photodiode 203. Signal charge (that is, holes or electrons) generated by the photodiode 203 is accumulated in a floating diffusion layer, which is a charge accumulation portion between the photodiode 203 and the source follower transistor 309.

Although not illustrated in FIG. 1E, the first to fourth floating diffusion layers 204, 205, 206, and 207 are connected to the photodiode 203. A switch can be provided between the photodiode 203 and the first to fourth floating diffusion layers 204, 205, 206, and 207. In accordance with a signal accumulation pulse from the control circuit 60, this switch switches a conductive state between the photodiode 203 and each of the first to fourth floating diffusion layers 204, 205, 206, and 207. This controls the start and stop of accumulation of signal charge in each of the first to fourth floating diffusion layers 204, 205, 206, and 207. The electronic shutter in the present embodiment has a mechanism for such exposure control.

The signal charges accumulated in the first to fourth floating diffusion layers 204, 205, 206, and 207 are read when a row selecting circuit 302 turns on gates of the row selecting transistors 308. During the reading, electrical current that flows from a source follower power source 305 into the source follower transistors 309 and source follower loads 306 is amplified in accordance with signal potentials in the first to fourth floating diffusion layers 204, 205, 206, and 207. Analog-to-digital conversion circuits 307 connected to respective columns convert analog signals due to the electrical current, read from vertical signal lines 304, into digital signal data. A column selecting circuit 303 reads the digital signal data for each column, and the digital signal data is output from the photodetector 30. After performing reading from one row, the row selecting circuit 302 and the column selecting circuit 303 perform reading from a next row, and thereafter, reading of information of signal charges in the floating diffusion layers in all rows is similarly performed. After reading all the signal charges, the control circuit 60 turns on the gates of the reset transistors 310 to thereby reset all the floating diffusion layers. This completes image capture of one frame. Thereafter, similarly, high-speed image capture of a frame is repeated, so that the photodetector 30 completes image capture of a series of frames.

Although an example of the CMOS-type photodetector 30 has been described in the present embodiment, the photodetector 30 may be another type of image capture element. The photodetector 30 may be, for example, a charge-coupled-device (CCD) type photodetector, a single-photon counting type element, or an amplification type image sensor (for example, an electron multiplying CCD (EMCCD) or intensified CCD (ICCD)).

Figure 1F:
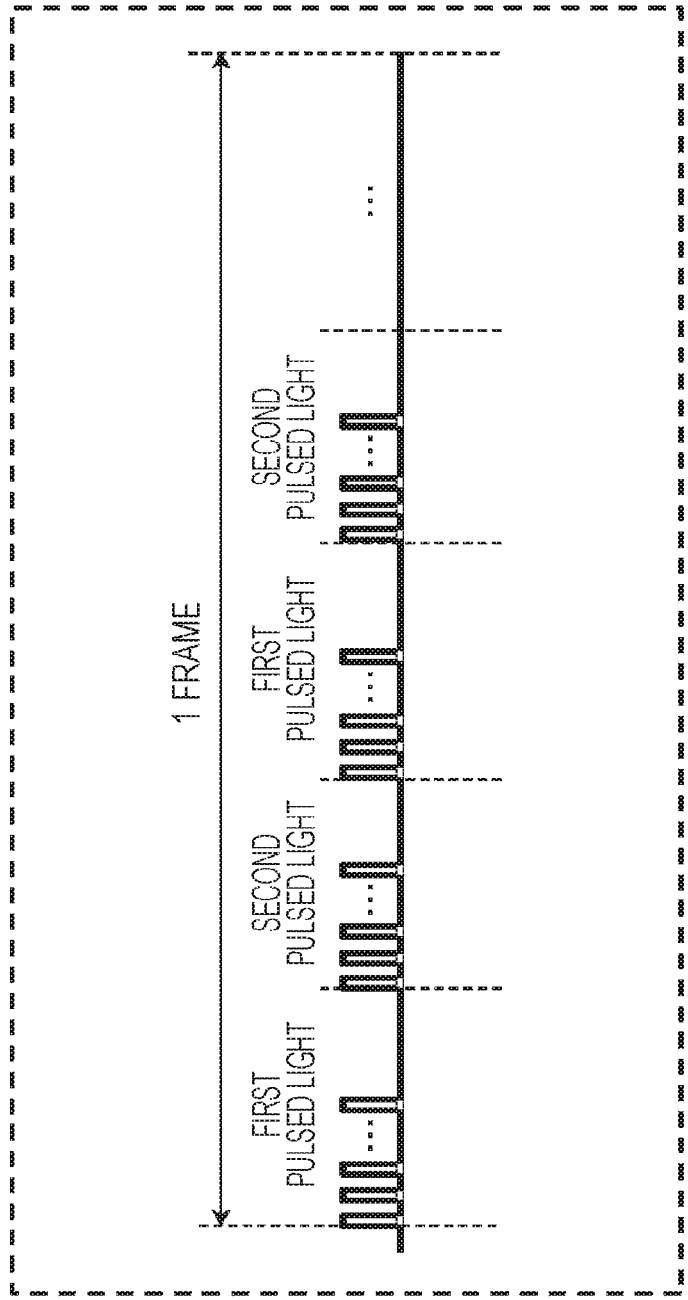
FIG. 1F is a diagram illustrating an example of an operation in one frame.

FIG. 1F is a diagram illustrating an example of an operation in one frame in the present embodiment. As illustrated in FIG. 1F, emission of the first pulsed light and emission of the second pulsed light may be alternately switched therebetween in one frame a plurality of times. Doing so makes it possible to reduce a time difference between the timings of acquiring detection images with two types of wavelength and makes it possible to perform photography with the first and second pulsed light at substantially the same time even for a user 1 who is moving.

In the present embodiment, the photodetector 30 detects both the surface reflection components I1 and the internal scattering components I2 of the pulsed light. First living-body information of the user 1 can be obtained from temporal or spatial changes in the surface reflection components I1. The first living-body information can be, for example, the pulse of the user 1. On the other hand, brain activity information, which is second living-body information, of the user 1 can be obtained from temporal or spatial changes in the internal scattering components I2.

The first living-body information may be obtained by a method different from a method for detecting the surface reflection components I1. For example, another type of detector that is different from the photodetector 30 may be utilized to obtain the first living-body information. In this case, the photodetector 30 detects only the internal scattering components I2. The other type of detector may be, for example, a radar or thermograph. The first living-body information can be, for example, at least one of the pulse, perspiration, breathing, and the body temperature of the user 1. The first living-body information is living-body information other than the brain activity information obtained by detecting the internal scattering components I2 of the pulsed light with which the head portion of the user 1 is illuminated. The "other than the brain activity information" in this case does not mean that the first living-body information does not include any information resulting from a brain activity. The first living-body information includes living-body information resulting from a biological activity different from a brain activity. The first living-body information is, for example, living-body information resulting from an autonomous or reflexive biological activity.

Herein, a signal indicating the first living-body information may be referred to as a "first biological signal" or simply as a "biological signal". Also, a signal indicating the brain activity information may be referred to as a "brain activity signal".

1-4. Output Device

The output device 40 includes, for example, at least one of a display and a speaker. The output device 40 outputs a result based on a biological reaction. When the stimulation device 10 includes a display or a speaker, it may function as the output device 40. The output device 40 can be, for example, a device including a display of a head-mounted device, a smartphone, or the like.

1-5. Input Device

The input device 50 receives an input of the user 1. The input of the user 1 is, for example, a response to a result output by the output device 40. The input device 50 can be, for example, a touch panel mounted on a smartphone or a tablet computer.

1-6. Control Circuit and Signal Processing Circuit

The control circuit 60 causes the stimulation device 10 to provide the stimulus 12, such as video or sound. The control circuit 60 may control at least one of the hue, chroma, and brightness of video or at least one of the sound quality and volume of sound.

The control circuit 60 adjusts a time difference between the light-emission timing of the pulsed light of the light source 20 and the shutter timing of the photodetector 30. This time difference may hereinafter be referred to as a "phase" or a "phase delay". The "light-emission timing" of the light source 20 refers to a timing at which the pulsed light emitted by the light source 20 starts rising. The "shutter timing" refers to a timing at which the exposure is started. The control circuit 60 may adjust the phase by changing the light-emission timing or may adjust the phase by changing the shutter timing.

The control circuit 60 may be configured so as to remove offset components from signals detected by the individual pixels in the photodetector 30. The offset components are signal components resulting from external light or ambient light, such as the sunlight or a fluorescent lamp. In a state in which the light source 20 does not emit light, that is, in a state in which driving of the light source 20 is turned off, the photodetector 30 detects signals to thereby estimate offset components resulting from ambient light or external light.

Based on a biological reaction measurement result obtained by the signal processing circuit 70, the control circuit 60 determines at least one emotion among a plurality of emotions included in a pre-defined emotion model. Details of a method for the emotion determination are described later.

The control circuit 60 causes the output device 40 to output at least one of an image and sound that are associated with the determined emotion group. The control circuit 60 may control at least one of hue, chroma, and brightness of the image or at least one of the sound quality and volume of the sound.

The control circuit 60 records, to a memory, data based on an input to the input device 50 which is performed by the user 1. The memory may be built into the living-body measurement system 100 or may be provided outside thereof.

The control circuit 60 can be, for example, a combination of a processor and a memory or an integrated circuit of a microcontroller or the like into which a processor and a memory are built. For example, in the control circuit 60, the processor executes a program recorded in the memory, to thereby perform adjustment of the light-emission timing and the shutter timing, the estimation of offset components, the removal of offset components, and so on.

The signal processing circuit 70 is a circuit for processing image signals output from the photodetector 30. The signal processing circuit 70 performs computational processing, such as image processing. The signal processing circuit 70 can be realized by, for example, a digital signal processor (DSP), a programmable logic device (PLD) such as a field programmable gate array (FPGA), or a combination of a central processing unit (CPU) or a graphics processing unit (GPU) and a computer program. The control circuit 60 and the signal processing circuit 70 may be an integrated circuit or may be separate individual circuits. Also, the signal processing circuit 70 may be, for example, a constituent element of an external device, such as a server computer provided at a remote location. In this case, the external device, such as a server computer, includes a communication means to transmit/receive data to/from the light source 20, the photodetector 30, and the control circuit 60.

The signal processing circuit 70 in the present embodiment can generate moving-image data indicating changes in skin-surface blood flow and cerebral blood flow over time, based on signals output from the photodetector 30. The signal processing circuit 70 may generate not only such moving-image data but also other information. For example, by synchronizing with other equipment, the signal processing circuit 70 may generate living-body information, such as a blood flow rate in the brain, a blood pressure, the saturation level of oxygen in blood, or a heart rate.

It has been known that there is a close relationship between changes in the cerebral blood flow rate or in-blood components, such as hemoglobin, and neural activities of the human. For example, when the activity of nerve cells changes in response to a change in the emotion of the human, the cerebral blood flow rate or components in blood change. Accordingly, when living-body information about changes in the cerebral blood flow rate, components in blood, or the like can be measured, the psychological state of the user 1 can be estimated. The psychological state of the user 1 means, for example, a mood (for example, pleasantness or unpleasantness), an emotion (for example, relief, anxiety, sadness, or anger), a health condition (for example, liveliness or fatigue), or a thermal sensation (for example, hot, cold, or muggy). Also, the psychological state includes indices that derive from those described above and that indicate the degrees of brain activities. Examples include the degree of proficiency, the degree of learning, the degree of concentration, and so on. The signal processing circuit 70 may estimate the psychological state, such as the degree of concentration, of the user 1, based on changes in the cerebral blood flow rate or the like, and may output a signal indicating a result of the estimation.

Figure 1G:
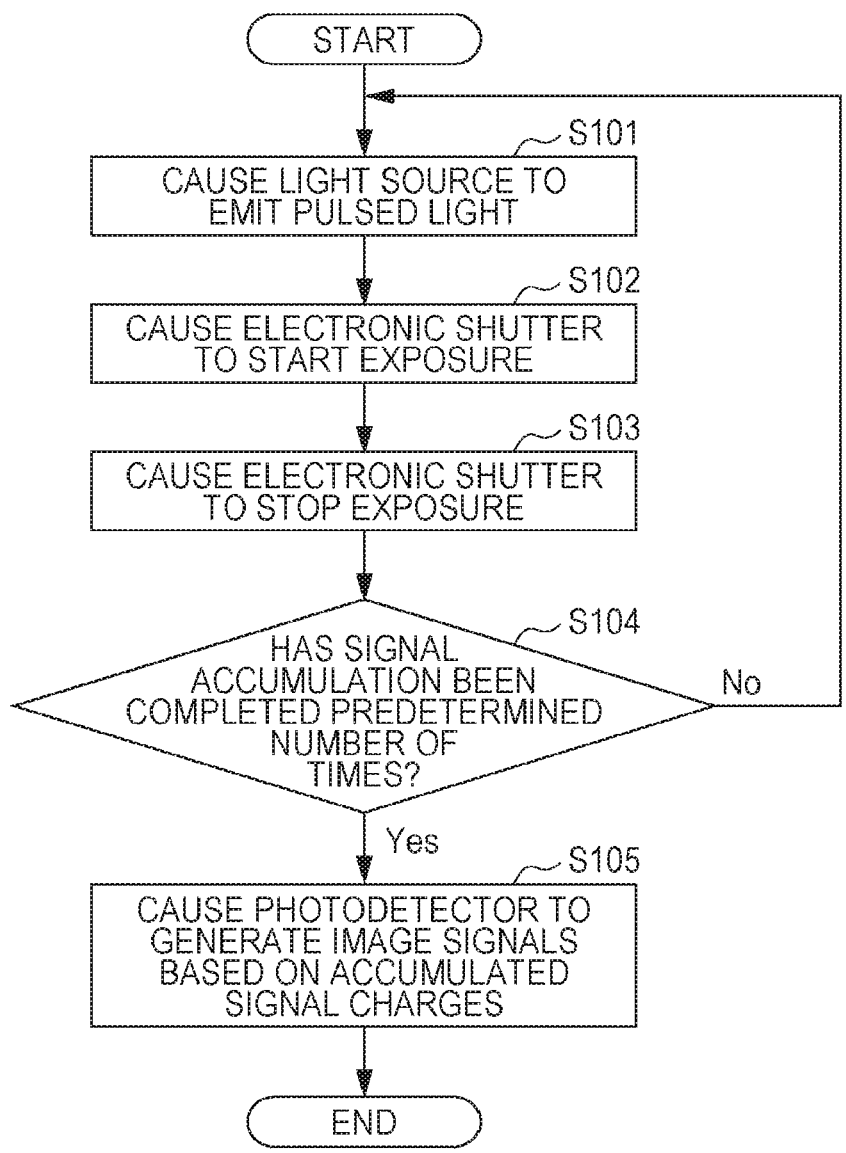
FIG. 1G is a flowchart illustrating an operation in a control circuit.

FIG. 1G is a flowchart illustrating an overview of an operation that the control circuit 60 performs on the light source 20 and the photodetector 30. The control circuit 60 generally executes the operation illustrated in FIG. 1G. Herein, a description will be given of an operation for only detecting the internal scattering components I2. In step S101, the control circuit 60 first causes the light source 20 to emit pulsed light for a predetermined time. At this point in time, the electronic shutter of the photodetector 30 is in a state in which the exposure is stopped. The control circuit 60 causes the electronic shutter to stop the exposure until a period in which part of the pulsed light is reflected on the surface of the user 1 and reaches the photodetector 30 is completed. Next, in step S102, the control circuit 60 causes the electronic shutter to start the exposure at a timing at which other part of the pulsed light reaches the photodetector 30 after scattering inside the user 1. After a predetermined time passes, in step S103, the control circuit 60 causes the electronic shutter to stop the exposure. Subsequently, in step S104, the control circuit 60 determines whether or not the number of times the above-described signal accumulation was executed has reached a predetermined number of times. If the result of this determination is No, steps S101 to S103 are repeated until the result of the determination is Yes. If the result of the determination in step S104 is Yes, in step S105, the control circuit 60 causes the photodetector 30 to generate signals indicating an image based on signal charges accumulated in the individual floating diffusion layers and to output the signals.

In the operation described above, components of light that scatters inside a measurement target can be detected with high sensitivity. The pluralities of light emissions and exposures are not essential and are performed as appropriate.

1-7. Others

The living-body measurement system 100 may include an image-forming optical system that forms a two-dimensional image of the user 1 on a light-receiving plane of the photodetector 30. An optical axis of the image-forming optical system is generally orthogonal to the light-receiving plane of the photodetector 30. The image-forming optical system may include a zoom lens. When the position of the zoom lens changes, the magnification factor of the two-dimensional image of the user 1 changes, and the resolution of the two-dimensional image on the photodetector 30 changes. Accordingly, even when the distance to the user 1 is large, the area to be measured can be magnified and be observed in detail.

Also, the living-body measurement system 100 may include, between the user 1 and the photodetector 30, a bandpass filter for passing only light in the band of wavelengths emitted from the light source 20 or light close to the band. This makes it possible to reduce influences of disturbance components of ambient light and so on. The bandpass filter is constituted by a multilayer film filter or an absorbing filter. The bandwidth of the bandpass filter may be given a width of about 20 to 100 nm, considering the temperature of the light source 20 and band shift that occurs upon oblique incidence on the filter.

Also, the living-body measurement system 100 may include a polarizer between the light source 20 and the user 1 and a polarizer between the photodetector 30 and the user 1. In this case, the polarization direction of the polarizer arranged adjacent to the light source 20 and the polarization direction of the polarizer arranged adjacent to the photodetector 30 have a crossed-Nicols relationship. This can prevent specular reflection components, that is, components whose incident angle and reflection angle are the same, of the surface reflection components I1 of the user 1 from reaching the photodetector 30. That is, it is possible to reduce the amount of light with which the surface reflection components I1 reach the photodetector 30.

2. Operation of Light Source and Photodetector

The living-body measurement system 100 in the present disclosure can perform detection through discrimination of the internal scattering components I2 from the surface reflection components I1. When the user 1 is a person, and the target portion is the forehead, the signal strength due to the internal scattering components I2 to be detected becomes very low. This is because, in addition to the light illumination with a very small amount of light that satisfies the laser safety standard, as described above, the amounts of light diffusion and absorption by the scalp, the cerebrospinal fluid, the skull, the grey matter, the white matter, and the blood flow are large. In addition, changes in the signal strength which are due to changes in the blood flow rate or the components flowing in blood during brain activity further correspond to a magnitude of one-several tenths and become very small. Accordingly, in the present embodiment, photography is performed without possibly mixing the surface reflection components I1 whose amount is thousands of times to tens of thousands of times of the signal components to be detected.

The following description will be given of an example of operations of the light source 20 and the photodetector 30 in the living-body measurement system 100 in the present embodiment.

As illustrated in FIG. 1A, when the light source 20 illuminates the user 1 with pulsed light, the surface reflection components I1 and the internal scattering components I2 occur. Some of the surface reflection components I1 and the internal scattering components I2 reach the photodetector 30. Since the internal scattering components I2 pass through the inside of the user 1 before the pulsed light reaches the photodetector 30 after being emitted from the light source 20, the optical path length is large compared with the surface reflection components I1. Accordingly, the time taken for the internal scattering components I2 to reach the photodetector 30 is delayed relative to the surface reflection components I1 on average.

Figure 2:
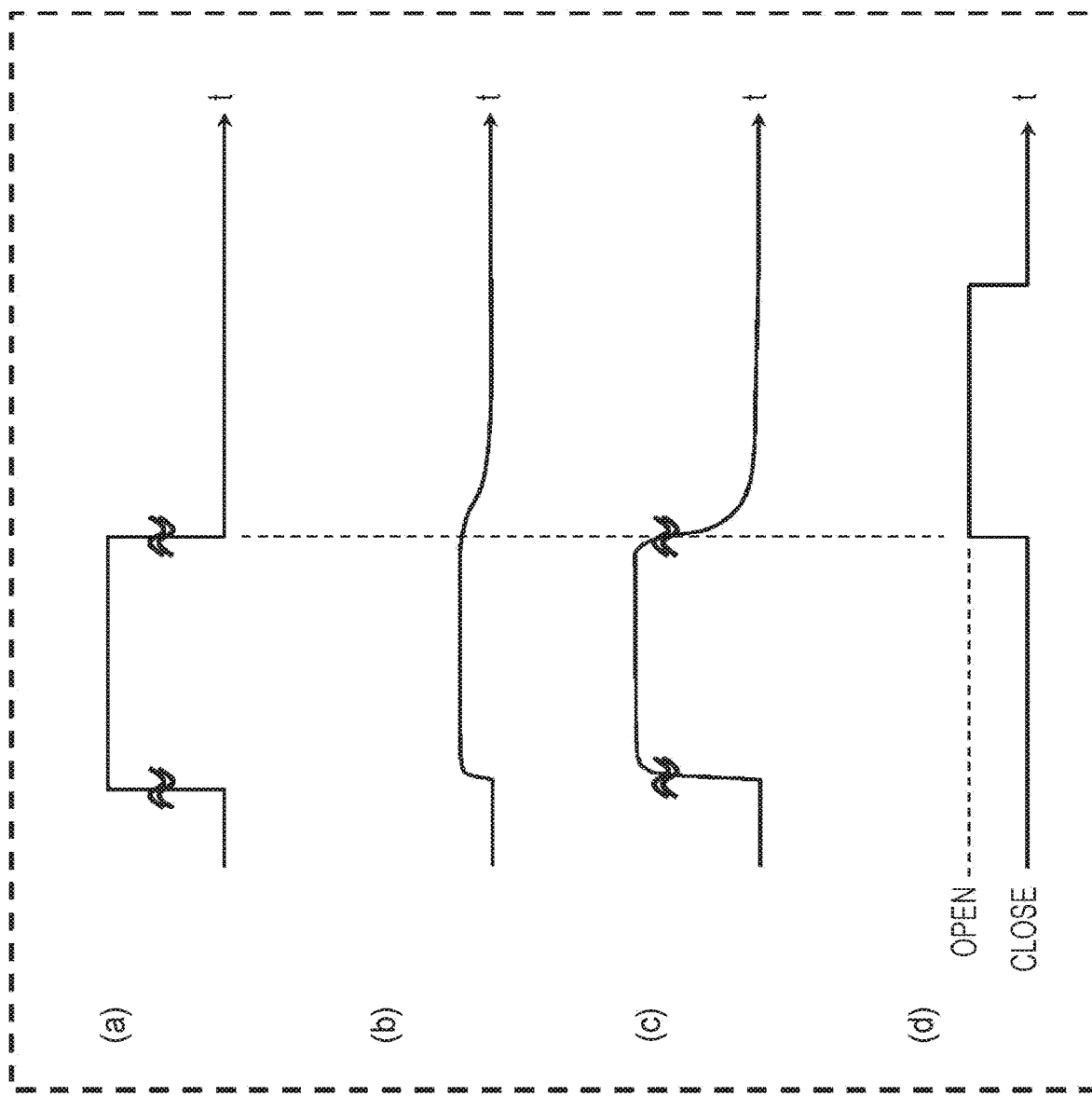
FIG. 2 is a diagram illustrating a method for detecting internal scattering components of pulsed light.

FIG. 2 is a diagram illustrating optical signals resulting from light that returns from the user 1 after rectangle pulsed light is emitted from the light source 20 and that reaches the photodetector 30. In waveforms (a) to (d), the horizontal axis represents time (t). In waveforms (a) to (c), the vertical axis represents an intensity, and in waveform (d), the vertical axis represents an open or close state of the electronic shutter. Waveform (a) indicates the surface reflection components I1. Waveform (b) indicates the internal scattering components I2. Waveform (c) indicates combined components of the surface reflection components I1 (*a*) and the internal scattering components I2 (*b*). As indicated by waveform (a), the surface reflection components I1 maintain a rectangle. On the other hand, since the internal scattering components I2 are a combination of light that has passed through various optical path lengths, they exhibit a characteristic like lingering at the rear end of the pulsed light, as indicated by waveform (b). That is, the internal scattering components I2 have a longer falling period than the surface reflection components I1. In order to extract the internal scattering components I2 from the optical signal having waveform (c), it is sufficient that the electronic shutter start exposure at or after the rear end of the surface reflection components I1, that is, at the time of or after falling of the surface reflection components I1, as indicated by waveform (d). The control circuit 60 adjusts the shutter timing. Since it is sufficient that the living-body measurement system 100 in the present disclosure be able to discriminate and detect the surface reflection components I1 and the internal scattering components I2 that reached a target deep part, as described above, the duration of the light pulses that are emitted and the shutter duration are arbitrary. Accordingly, unlike a method using a typical streak camera, the detection can be realized with a simple configuration, and cost can be significantly reduced.

In waveform (a) in FIG. 2, the rear end of the surface reflection components I1 falls perpendicularly. In other words, the time from when the surface reflection components I1 start falling until the surface reflection components I1 end the falling is zero. In practice, however, there are cases in which the rear end of the surface reflection components I1 does not fall perpendicularly, since the falling portion of the waveform of the pulsed light radiated by the light source 20 is not completely perpendicular, minute bumps and pits are present at the surface of the user 1, or diffusion occurs in the epidermis. Also, since the user 1 is an opaque object, the amount of light of the surface reflection components I1 becomes much larger than that of the internal scattering components I2. Accordingly, even when the rear end of the surface reflection components I1 protrudes from its perpendicular falling position, there is a possibility that the internal scattering components I2 are hidden by the rear-end portion of the surface reflection components I1. There are also cases in which ideal binary reading as indicated by waveform (d) in FIG. 2 cannot be performed due to a time delay involved in electron transfer in the reading period of the electronic shutter. Accordingly, the control circuit 60 may slightly delay the shutter timing of the electronic shutter relative to the point in time that is immediately after falling of the surface reflection components I1. For example, the control circuit 60 may delay the shutter timing by about 0.5 to 5 ns. Instead of adjusting the shutter timing of the electronic shutter, the control circuit 60 may adjust the light-emission timing of the light source 20. The control circuit 60 adjusts a time difference between the shutter timing of the electronic shutter and the light-emission timing of the light source 20. For measuring changes in the blood flow rate or components flowing in blood in a contactless manner during brain activity, when the shutter timing is overly delayed, the amount of the internal scattering components I2 which is inherently small decreases further. Thus, the shutter timing may be held in the vicinity of the rear end of the surface reflection components I1. Since the time delay due to diffusion in the user 1 is 4 ns, the maximum amount of delay of the shutter timing is about 4 ns.

The amount of detected light of the internal scattering components I2 may be amplified by the light source 20 emitting pulsed light a plurality of times and performing exposure a plurality of times on the individual pulsed light at a shutter timing with the same phase.

Instead of or in addition to arranging the bandpass filter between the user 1 and the photodetector 30, the control circuit 60 may estimate offset components by performing photography with the same exposure time in a state in which the light source 20 does not emit light. A difference between the estimated offset components and signals detected from the pixels of the photodetector 30 is removed from the detected signals. This makes it possible to eliminate dark-current components that occur on the photodetector 30.

The internal scattering components I2 include internal feature information of the user 1, for example, cerebral blood flow information. The amount of light absorbed by blood in response to variations over time in the cerebral blood flow rate of the user 1 changes, and correspondingly, the amount of light detected by the photodetector 30 also increases/decreases. Accordingly, monitoring the internal scattering components I2 makes it possible to estimate the state of brain activities from the cerebral blood flow rate of the user 1. Herein, of signals output from the photodetector 30, signals indicating the internal scattering components I2 may be referred to as "brain activity signals". The brain activity signals can include increase/decrease information of the cerebral blood flow of the user 1.

Next, a description will be given of an example of a method for detecting the surface reflection components I1. The surface reflection components I1 include surface feature information of the user 1. Examples include blood flow information of the face and the scalp. The photodetector 30 detects the surface reflection components I1 of optical signals that return to the photodetector 30 after the pulsed light emitted by the light source 20 reaches the user 1.

FIG. 3A illustrates one example of a timing chart for detection of the surface reflection components I1. In order to detect the surface reflection components I1, for example, the shutter may be opened before the pulsed light reaches the photodetector 30, and the shutter may be closed before the rear end of the pulsed light reaches the photodetector 30, as illustrated in FIG. 3A. Controlling the shutter in such a manner makes it possible to reduce mixing of the internal scattering components I2. This also makes it possible to increase the rate of light that passes through the vicinity of the surface of the user 1. In particular, the timing of closing the shutter may be immediately after the light reaches the photodetector 30. Doing so makes it possible to perform signal detection in which the rate of the surface reflection components I1 whose optical path lengths are relatively small are increased. Obtaining signals of the surface reflection components I1 makes it possible to detect the pulse of the user 1 or the oxygenation level of the facial blood flow. As another method for obtaining the surface reflection components I1, the photodetector 30 may obtain the entire pulsed light, or continuous light may be radiated from the light source 20 and be detected.

FIG. 3B illustrates one example of a timing chart for detection of the internal scattering components I2. Opening the shutter in a period in which the rear-end portion of each pulse reaches the photodetector 30 makes it possible to obtain signals of the internal scattering components I2.

The surface reflection components I1 may be detected by a device other than the living-body measurement system 100 that obtains the internal scattering components I2. A device that is independent from the device that obtains the internal scattering components I2 or another device, such as a pulse wave meter or a Doppler blood flowmeter, may be used. When another device is to be used, it will be used considering timing synchronization between devices, light interference, and alignment of a portion to be detected. As in the present embodiment, when time-shared image capture using the same camera or the same sensor is performed, temporal and spatial displacement is less likely to occur. When signals of both the surface reflection components I1 and the internal scattering components I2 are obtained using the same sensor, components to be obtained may be switched for each frame, as illustrated in FIGS. 3A and 3B. Alternatively, components to be obtained may be alternately switched within one frame at high speed, as described above with reference to FIGS. 1D to 1F. In this case, it is possible to reduce a detection time difference between the surface reflection components I1 and the internal scattering components I2.

In addition, respective signals of the surface reflection components I1 and the internal scattering components I2 may be obtained using light having two wavelengths. For example, pulsed light having two wavelengths of 750 nm and 850 nm may be utilized. Doing so makes it possible to calculate changes in the concentration of oxygenated hemoglobin and changes in the concentration of deoxygenated hemoglobin from changes in the amounts of light detected with the respective wavelengths. When the surface reflection components I1 and the internal scattering components I2 are each obtained with two wavelengths, for example, a method in which four types of charge accumulation are switched at high speed within one frame can be utilized, as described above with reference to FIGS. 1D to 1F. With such a method, it is possible to reduce temporal displacement of detection signals.

The living-body measurement system 100 radiates pulsed near-infrared or visible light to the forehead of the user 1 and can detect his or her pulse or changes in the amount of oxygenated hemoglobin in the scalp or the face from changes in the surface reflection components I1 over time. The light source 20 for obtaining the surface reflection components I1 emits the near-infrared or the visible light. With the near-infrared, the measurement can be performed regardless of the time of day or night. When the pulse is measured, visible light having higher sensitivity may be used. In the daytime, sunlight, which is external light, or an indoor light source may be used for lighting. When the amount of light is not sufficient, it may be reinforced with a dedicated light source. The internal scattering components I2 include light components that reached the brain. Measuring changes in the internal scattering components I2 over time makes it possible to measure increases/decreases in the cerebral blood flow over time.

Since the light that reached the brain also passes through the scalp and the surface of the face, variations in and, variations in blood flow in the scalp and the face are also superimposed and are detected. In order to eliminate or reduce influences of the variations, the signal processing circuit 70 performs processing for subtracting the surface reflection components I1 from the internal scattering components I2 detected by the photodetector 30. Doing so makes it possible to obtain pure cerebral blood flow information excluding scalp and face blood flow information. A method for the subtraction may be, for example, a method for subtracting values, obtained by multiplying the signals of the surface reflection components I1 by one or more coefficients determined considering the optical path length differences, from the signals of the internal scattering components I2. The coefficient(s) can be calculated, for example, through a simulation or experiment, based on the average value of optical constants of the head portions of general people. Such subtraction processing can be particularly easily performed using the same camera or sensor when measurement is performed using light having the same wavelength. This is because temporal and spatial displacement can be easily reduced, and characteristics of scalp blood flow components included in the internal scattering components I2 and characteristics of the surface reflection components I1 can be easily matched.

The skull exists between the brain and the scalp. Thus, the two-dimensional distribution of the cerebral blood flow and the two-dimensional distribution of the blood flow in the scalp and the face are independent from each other. Accordingly, based on signals detected by the photodetector 30, the two-dimensional distribution of the internal scattering components I2 and the two-dimensional distribution of the surface reflection components I1 may be separated using a statistical scheme, such as independent component analysis or primary component analysis.

3. Determination of State of User Before Measurement

Next, a description will be given of an example of a method for estimating the emotion of the user 1 by using the above-described living-body measurement system 100.

As described above, the signal processing circuit 70 calculates a scalp blood flow rate B1 and a cerebral blood flow rate B2 of the user 1, respectively, from the surface reflection components I1 and the internal scattering components I2. The scalp blood flow rate is adjusted based on flow rate changes caused by dilation and constriction of blood vessels in the scalp. The dilation and constriction of blood vessels are controlled by autonomic nerves. The autonomic nerves are mainly sympathetic nerves. The sympathetic nerves are activated during affective response, sleepiness, or stress response to regulate the facial blood flow rate.

In the present embodiment, the signal processing circuit 70 estimates a state that derives from the autonomic nerves of the user 1 from the surface reflection components I1, which are blood flow information that derives from the scalp, and estimates a state that derives from the cerebral nerves from the internal scattering components I2, which are cerebral blood flow information that derives from the brain. The signal processing circuit 70 further estimates states of the user 1 from those two pieces of information.

The activation of the autonomic nerves is controlled according to physical and mental states, such as an emotion, stress, and physical condition of the human. Accordingly, the blood flow rate of the face is considered to represent the physical and mental states of the human.

On the other hand, the cerebral nerves become active in order to control brain functions, such as cognition, decision, and affect. Upon activation of the cerebral nerves, the blood flow rate of the brain changes. Thus, the cerebral blood flow, particularly, the cerebral blood flow in the forehead portion corresponding to the prefrontal area of the brain, is considered to reflect the state of concentration.

That is, two pieces of information on the facial and cerebral blood flows are thought to reflect different states of the human. In the present embodiment, the physical and mental states of the human are estimated based on those two pieces of information.

For measuring the cerebral blood flow in the frontal cortex in measurement of a cognitive function of the brain, there are cases in which before the measurement, the state of the user 1 is determined by referring to the scalp blood flow.

FIG. 4 is a flowchart illustrating one example of processing for determining the state of the user 1 before measurement in the present embodiment.

In step S201, the control circuit 60 causes the light source 20 to illuminate the forehead portion of the user 1 with pulsed light and causes the photodetector 30 to measure the surface reflection components I1. During the measurement, the control circuit 60 records the number of measurements. In step S202, by using the signal processing circuit 70, the control circuit 60 calculates a scalp blood flow rate B1 from values of the surface reflection components I1. In step S203, the control circuit 60 determines whether the number of measurements is smaller than or equal to a prescribed value N. In step S204, the control circuit 60 compares the calculated scalp blood flow rate B1 with the range of scalp blood flow rates in an average rest state of the user 1, the scalp blood flow rates being pre-accumulated in a recording medium as a database. When B1 is within the range, the control circuit 60 determines that the user 1 is in a rest state. In this case, in step S205, in order to evaluate cognitive functions, the control circuit 60 presents a task by using the stimulation device 10 and starts measuring the cognitive functions. On the other hand, when B1 is not within the range in step S204, the control circuit 60 repeats steps S201 to S204.

When the number of measurements reaches N in step S203, in step S206, the control circuit 60 determines whether the Nth B1 is within the range of an "average value of B1 of the N−1 measurements performed up to this point"±a "standard deviation". When the Nth B1 is within the range, the control circuit 60 presents a task by using the stimulation device 10 in step S205. When the Nth B1 is not within the range in step S206, the control circuit 60 determines that the user 1 is not in a measurable state. In this case, in step S207, the control circuit 60 causes the output device 40 to output, to the user 1, an announcement for prompting deep breathing or relaxation and suspends the measurement.

4. Creation of Emotion/Arousal-Level Map

The facial blood flow is controlled by the autonomic nervous system that exists in the face. The facial blood flow plays an important role in body temperature regulation. The autonomic nervous system is regulated by, particularly, the hypothalamus in the brain. At the same time, upon receiving information from the limbic system, the hypothalamus regulates an autonomic nerve that suits the information. It has been reported that the amygdalae included in the limbic system are particularly activated by a negative affect. Thus, it is expected that affective responses can be measured via autonomic nerve control as changes in the facial blood flow.

Non-Patent Document 1 discloses measuring changes in the facial blood flow of a target person while he or she is viewing a moving image. The moving image elicits emotions, such as astonishment, sadness, fear, and excitement. The measurement uses a laser-speckle blood flowmeter. According to Non-Patent Document 1, the facial blood flow of the user 1 decreases significantly through viewing the moving image. Also, Peter D. Drummond et al. "The effect of expressing anger on cardiovascular reactivity and facial blood flow in Chinese and Caucasians" Psychophysiol., 38: 190-196, 2001, which is herein referred to as "Non-Patent Document 3, discloses measuring changes in the facial blood flow, by paying attention to the emotion of "anger". According to Non-Patent Document 3, when the emotion of "anger" is expressed, the facial blood flow increases by about 10%. Thus, detecting changes in the facial blood flow makes it possible to estimate the emotion of the user 1.

When the results of the preceding studies described above are summarized, the emotion of anger, astonishment, or the like increases the facial blood flow, and unpleasantness, sadness, or fear reduces the facial blood flow.

Next, a description will be given of Russell's circumplex model, which is often used as an index for classifying emotions.

Figure 5:
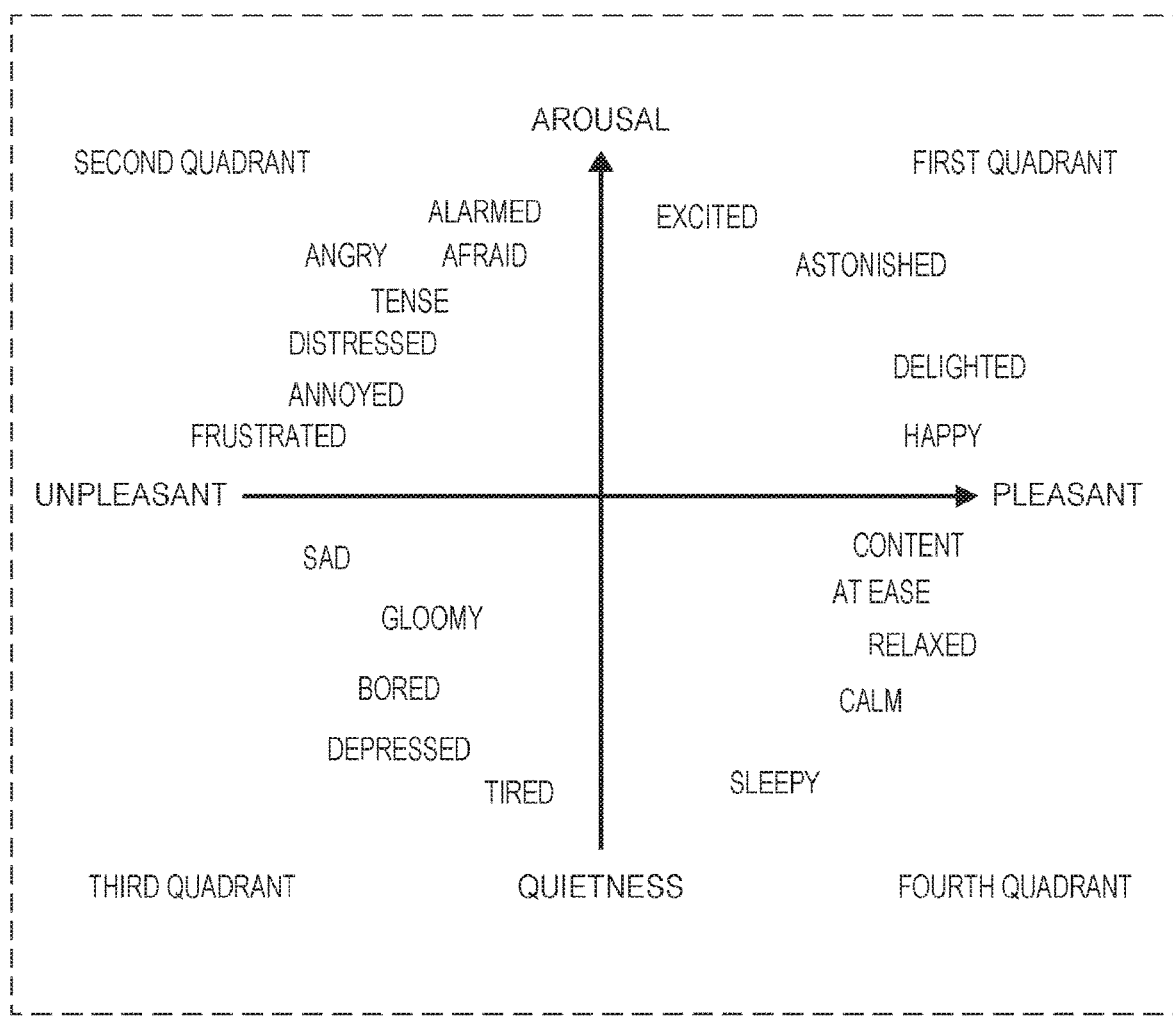
FIG. 5 is a diagram schematically illustrating Russell's circumplex model.

FIG. 5 is a diagram schematically illustrating Russell's circumplex model. In Russell's circumplex model, the emotions are classified into four quadrants by two axes for "pleasantness-unpleasantness" and an arousal level "arousal-calmness".

When Russell's circumplex model illustrated in FIG. 5 and emotions estimated based on changes in the facial blood flow are overlaid, the result described below is obtained. Of the emotions that reduce the facial blood flow, the "astonishment" and the "excitement" exist in the first quadrant, the "fear" exists in the second quadrant, and the "sadness" exists in the third quadrant. Meanwhile, the "anger" that increases the facial blood flow exists in the second quadrant. Thus, the emotions that are due to an increase/decrease in the facial blood flow and that can be estimated do not correspond to the four quadrants in Russell's circumplex model.

Meanwhile, the cerebral blood flow in the prefrontal area is known to increase during control of cognition, intent, or emotion. For example, an increase in the blood flow in the prefrontal area during execution of a task for checking the cognitive functions has been confirmed by a method, such as functional near-infrared spectroscopy (fNIRS) or functional magnetic resonance imaging (fMRI). The task for checking the cognitive functions is, for example, a verbal fluency task or an N-back task. It is determined that the user 1 is addressing the task with more concentration thereon, as an increase in the cerebral blood flow gets larger.

Meanwhile, it has been pointed out that when a similar cognitive task is repeated, the score of the cognitive task improves, but the cerebral blood flow decreases. This is considered to be due to the following reason. When a task is repeatedly executed, means for efficiently executing the task is mastered. In addition, changes occur in an active area in the brain to cause cerebral function localization by which much load is not applied to the prefrontal area.

Conversely, it has been reported that the cerebral blood flow decreases due to sleepiness.

In view of the above-described result, an attitude of addressing the task, that is, the degree of concentration, can be determined in accordance with an increase/decrease in the cerebral blood flow. Specifically, it can be estimated that the degree of concentration on the task is high, in response to an increase in the cerebral blood flow, and it can be estimated that the subject person is feeling sleepy and lacking concentration on the task, in response to a decrease in the cerebral blood flow.

In the living-body measurement system 100 in the present embodiment, the affect of the user 1 is estimated using the facial blood flow, and the degree at which the user 1 addresses a task is evaluated using the cerebral blood flow.

As described above, emotions estimated based on the increase/decrease in the blood flow do not correspond to the four quadrants in Russell's circumplex model illustrated in FIG. 5. Accordingly, in the present embodiment, classification in which an increase/decrease in the facial blood flow and an increase/decrease in the cerebral blood flow are two axes, the classification being different from Russell's circumplex model, makes it possible to estimate the emotion of the user 1.

Figure 6:
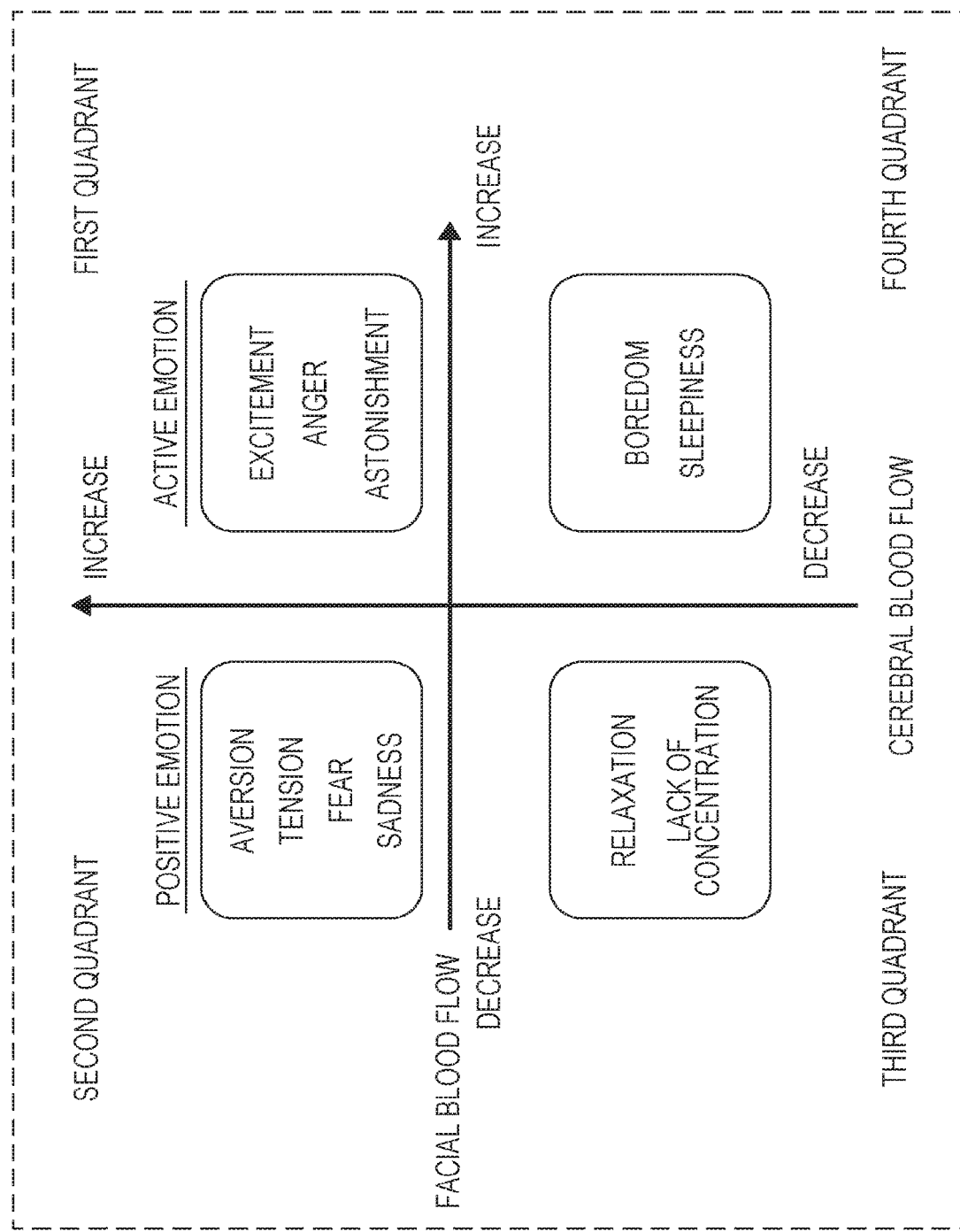
FIG. 6 is a diagram schematically illustrating an emotion/arousal-level map.

FIG. 6 is a diagram schematically illustrating an emotion/arousal-level map in the present embodiment. The "emotion/arousal-level map" indicates four emotion groups classified according to an increase/decrease in the facial blood flow and an increase/decrease in the cerebral blood flow. The horizontal axis represents an increase/decrease in the facial blood flow, and the vertical axis represents an increase/decrease in the cerebral blood flow. The emotion/arousal-level map is one example of an emotion model in the present disclosure.

The excitement, anger, and astonishment in a first quadrant are assumed to be a first emotion group. The excitement, anger, and astonishment correspond to active emotions. Aversion, fear, sadness, and tension (referred to as a "passive emotion") in a second quadrant are assumed to be a second emotion group. The aversion, fear, sadness, and tension correspond to passive emotions. Relaxation and lack of concentration in a third quadrant are assumed to be a third emotion group. Boredom and sleepiness in a fourth quadrant are assumed to be a fourth emotion group. Herein, the classification of four emotion groups in the first to fourth quadrants is referred to as the "emotion/arousal-level map".

Next, a description will be given of a procedure for classifying the emotion of the user 1 into any of the four emotion groups.

Figure 7:
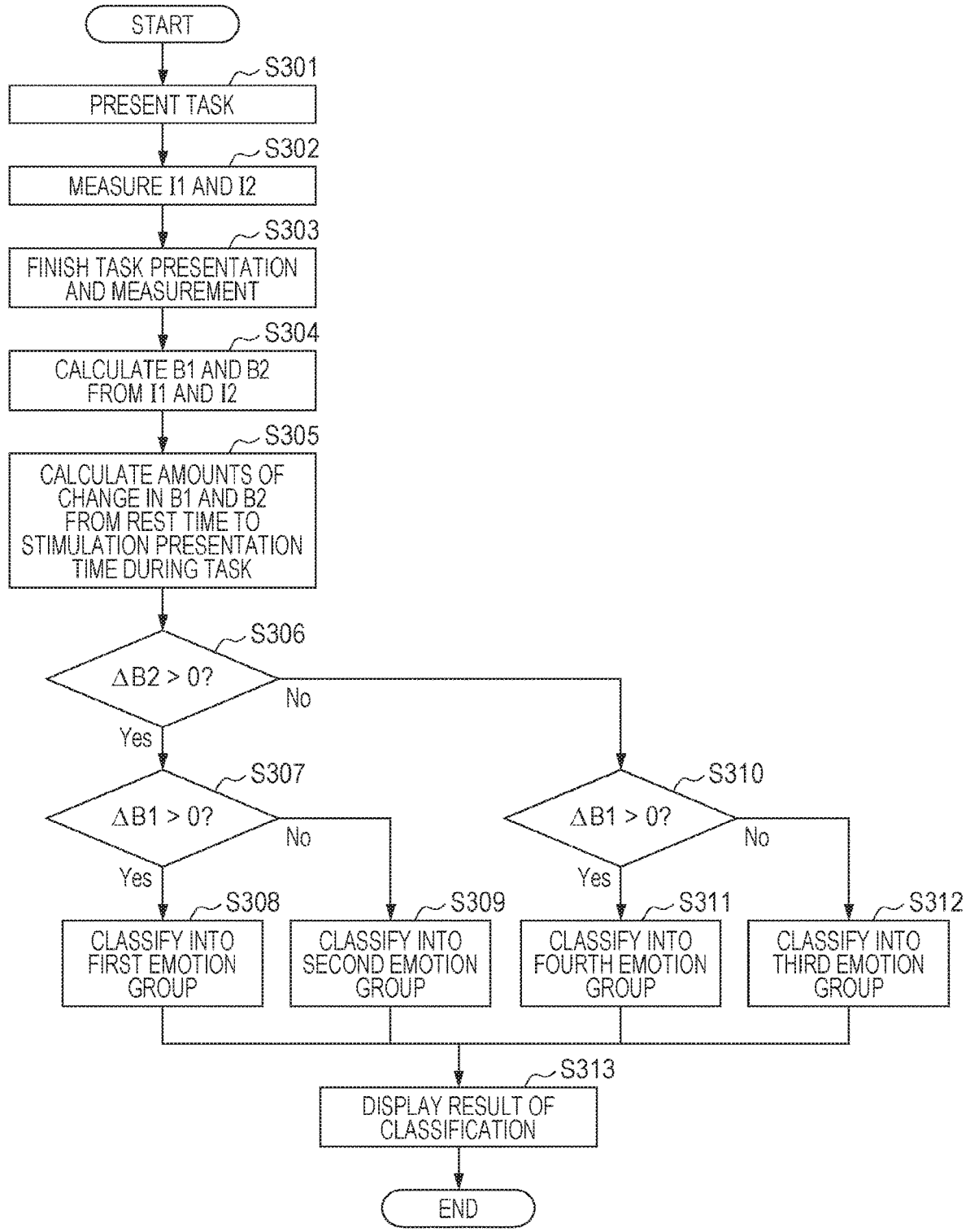
FIG. 7 is a flowchart illustrating one example of processing for classifying the emotion of the user into any of four emotion groups.

FIG. 7 is a flowchart illustrating one example of processing for classifying the emotion of the user 1 into any of the four emotion groups.

In step S301, the control circuit 60 presents a task to the user 1 by using the stimulation device 10. In step S302, the control circuit 60 causes the light source 20 to illuminate the user 1 with pulsed light during the presentation of the task and causes the photodetector 30 to measure the surface reflection components I1 and the internal scattering components I2 at regular time intervals. In step S303, the control circuit 60 finishes the task presentation, then suspends the illumination of the pulsed light, and finishes the measurement. In step S304, the control circuit 60 causes the signal processing circuit 70 to calculate the scalp blood flow rate B1 and the cerebral blood flow rate at each point in time B2 from I1 and I2.

A time slot in which load is applied to the user 1, like a time slot during which a task is presented, is defined as a "stimulation time". A time slot in which the user 1 is urged to rest without provision of a stimulus is defined as a "rest time". A scalp blood flow rate and a cerebral blood flow rate in the rest time are given by $B1_{Rest}$ and $B2_{Rest}$, respectively. A scalp blood flow and a cerebral blood flow rate in the stimulation time are given by $B1_{stimuli}$ and $B2_{stimuli}$, respectively. The amount of change in the scalp blood flow from the rest time to the stimulation time and the amount of change in the cerebral blood flow from the rest time to the stimulation time are given by $\Delta B1 = B1_{stimuli} - B1_{Rest}$ and $\Delta B2 = B2_{stimuli} - B2_{Rest}$, respectively. $B1_{Rest}$, $B2_{Rest}$, $B1_{stimuli}$, and $B2_{stimuli}$ each represent a representative value of the blood flow rate in the corresponding time slot. How the representative value is determined can be arbitrarily selected depending on the measurement target or the type of task. For example, the representative value may be an average value of all time slots for each representative value or may be a median, maximum value, or minimum value thereof. In accordance with the polarity of $\Delta B1$ and the polarity of $\Delta B2$, the control circuit 60 classifies the emotion of the user 1 into any of four emotion groups described below. In other words, the control circuit 60 determines one emotion group, based on a combination of $\Delta B1$ and $\Delta B2$.

In step S306, the control circuit 60 determines whether $\Delta B2$ is positive. If $\Delta B2$ is positive, in step S307, the control circuit 60 determines whether $\Delta B1$ is positive. If $\Delta B1$ is positive, in step S308, the control circuit 60 classifies the emotion of the user 1 into the first emotion group. If $\Delta B1$ is not positive, in step S309, the control circuit 60 classifies the emotion of the user 1 into the second emotion group.

If $\Delta B2$ is not positive in step S306, in step S310, the control circuit 60 determines whether $\Delta B1$ is positive. If $\Delta B1$ is positive, in step S311, the control circuit 60 classifies the emotion of the user 1 into the fourth emotion group. If $\Delta B1$ is not positive, in step S312, the control circuit 60 classifies the emotion of the user 1 into the third emotion group.

In step S313, the control circuit 60 displays a result of the classification by using the output device 40.

Although, in the above-described example, the control circuit 60 classifies the emotion of the user 1 in accordance with the polarity of $\Delta B1$ and the polarity of $\Delta B2$, the classification is not limited thereto. For example, the emotion of the user 1 may be classified as described below.

For $\Delta B1 > C11$ and $\Delta B2 > C12$, the control circuit 60 classifies the emotion of the user 1 into the first emotion group. In this case, C11 and C12 are values greater than 0.

For $\Delta B1 < C21$ and $\Delta B2 > C22$, the control circuit 60 classifies the emotion of the user 1 into the second emotion group. In this case, C21 is a value smaller than 0, and C22 is a value greater than 0.

For $\Delta B1 < C31$ and $\Delta B2 < C32$, the control circuit 60 classifies the emotion of the user 1 into the third emotion group, where C31 and C32 are values smaller than 0.

For $\Delta B1 > C41$ and $\Delta B2 < C42$, the control circuit 60 classifies the emotion of the user 1 into the fourth emotion group. In this case, C41 is a value greater than 0, and C42 is a value smaller than 0.

When the emotion does not belong to any of the four emotion groups, it may be determined the absolute value of the amount of change in $\Delta B1$ and/or the absolute value of the amount of change in $\Delta B2$ are/is small, and re-measurement may be performed.

5. Subjective Evaluation of Emotion

Next, a description will be given of a method in which the emotion of the user 1 during execution of a task is estimated by subjective evaluation of the user 1.

Figure 8:
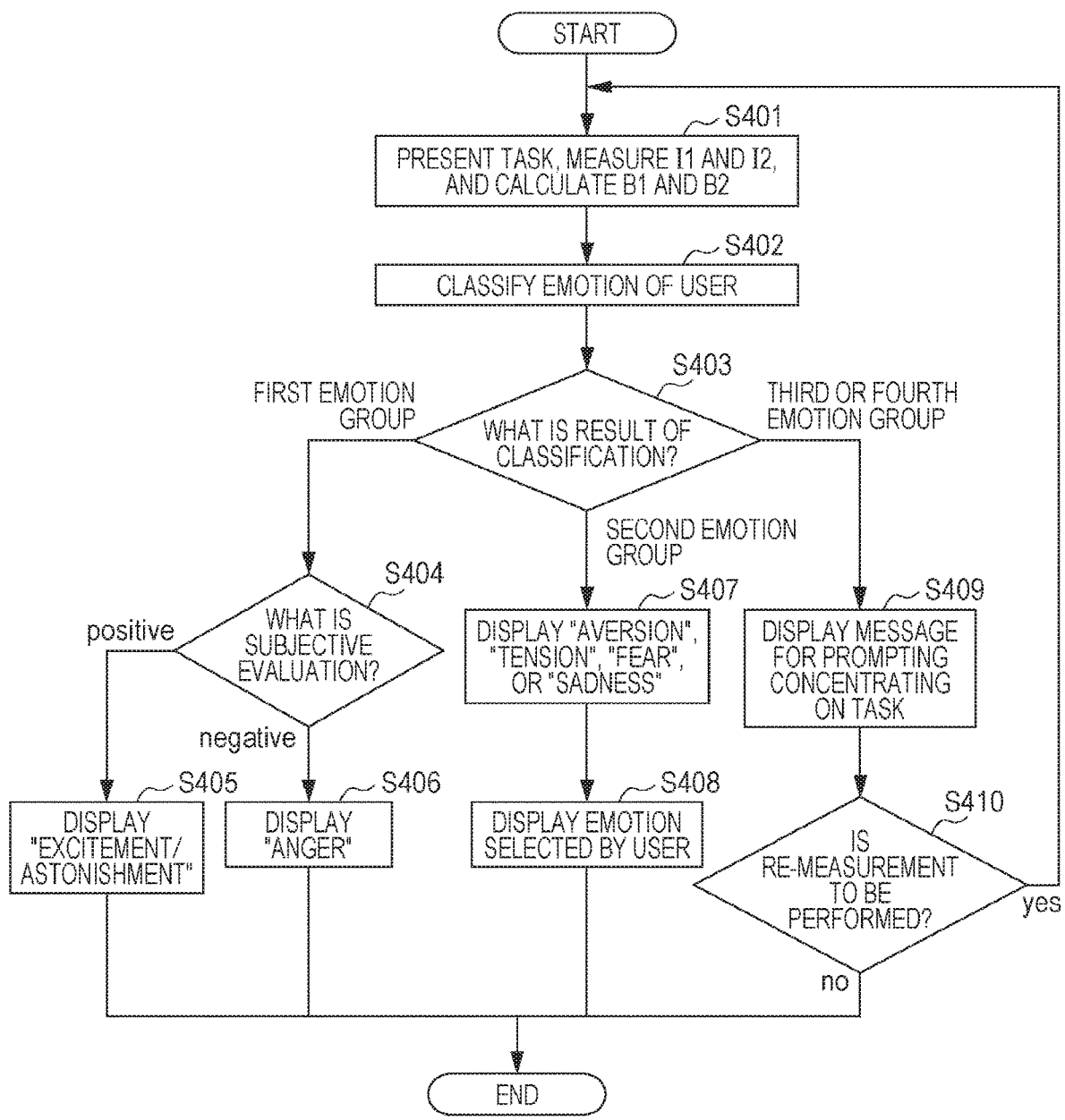
FIG. 8 is a flowchart illustrating one example of processing for estimating the emotion of the user during execution of a task.

FIG. 8 is a flowchart illustrating one example of processing for estimating the emotion of the user 1 during execution of a task.

In step S401, the control circuit 60 causes the stimulation device 10 to present a task to the user 1 and causes the photodetector 30 to measure the surface reflection components I1 and the internal scattering components I2. The control circuit 60 further causes the signal processing circuit 70 to calculate the scalp blood flow rate B1 and the cerebral blood flow rate B2. The processing in step S401 is the same as the processing in steps S301 to S305 illustrated in FIG. 7.

In step S402, the control circuit 60 classifies the emotion of the user 1, based on the emotion/arousal-level map illustrated in FIG. 6. The processing in step S402 is the same as the processing in steps S306 to S312 illustrated in FIG. 7.

In step S403, the control circuit 60 displays a result of the classification. The processing in step S403 is the same as the processing in step S313 illustrated in FIG. 7.

When the emotion of the user 1 is classified into any of the emotion groups, the control circuit 60 uses the output device 40 to query the user 1 about subjective evaluation. The subjective evaluation is, for example, evaluation as to whether at least one emotion classified into the determined emotion group corresponds to the actual emotion of the user 1. The control circuit 60 causes the output device 40 to output an image and/or sound for making the above-described query.

When the emotion of the user 1 is classified into the first emotion group in step S403, the process proceeds to step S404. In step S404, the control circuit 60 causes the output device 40 to display a question for making the user 1 execute the subjective evaluation. The contents of the question may be, for example, merely asking whether the emotion was a positive emotion or a negative emotion, like "Was your emotion during execution of the task was positive? or negative?". If the user 1 answers that his or her emotion was positive, that is, a positive emotion, the process proceeds to step S405. In step S405, the control circuit 60 causes the output device 40 to display an image indicating that the emotion of the user 1 during the execution of the task was "excitement/astonishment". If the user 1 answers that his or her emotion was negative, that is, a negative emotion, the process proceeds to step S406. In step S406, the control circuit 60 causes the output device 40 to display an image indicating that the emotion of the user 1 during the execution of the task was "anger". Instead of making the query as to whether the emotion of the user 1 was a positive emotion or a negative emotion, in step S404, the control circuit 60 may cause the output device 40 to display choices for selecting any of "excitement", "astonishment", and "anger".

If the emotion of the user 1 is classified into the second emotion group in step S403, the process proceeds to step S407. In step S407, the control circuit 60 causes the output device 40 to display choices of "aversion", "tension", "fear", and "sadness". The user 1 performs subjective evaluation and selects one of the emotions. The user 1 inputs the selected emotion by using the input device 50. In step S408, the control circuit 60 causes the output device 40 to display the emotion selected by the user 1.

When the emotion of the user 1 is classified into the third or fourth emotion group in step S403, the process proceeds to step S409. In this case, it is possible to estimate that the user 1 was in the state of relaxation, lack of concentration, boredom, or sleepiness during the execution of the task. Hence, in step S409, the control circuit 60 causes the output device 40 to display a message for prompting concentrating on the task. Subsequently, in step S410, the control circuit 60 causes the output device 40 to display an image for querying the user about whether or not re-measurement is to be performed. If the re-measurement is to be performed, the control circuit 60 executes step S401 again.

In the above-described processing, the attitude of the user 1 addressing the task and the emotion of the user 1 during the execution of the task can be estimated with high accuracy, based on two pieces of information about the facial blood flow and the cerebral blood flow.

Based on the result of the subjective evaluation of the user 1, the control circuit 60 may associate the stimulus 12 and the emotion of the user 1. For example, when the user 1 performs the above-described subjective evaluation by using the input device 50, the control circuit 60 may record data indicating an association between the stimulus 12 and the above-described at least one emotion to a memory. For example, an identifier indicating the subjective evaluation of the user 1 may be given to data indicating the stimulus 12. When the stimulus 12 is video or sound content, information indicating the result of the subjective evaluation of the user 1 may be added to data of the content and be recorded.

6. System in Which Content is Provided

The above-described living-body measurement system 100 can be used in, for example, a system in video or sound content is provided through a network, such as the Internet. Such a system can include, for example, various types of computer, such as a server computer operated by a business operator and a personal computer, a smartphone, or a tablet computer in the possession of a user. For example, a large number of users can exist throughout the world. Each of the users utilizes the above-described living-body measurement system 100 that estimates an emotion. For example, by using a computer, such as a smartphone, each user requests the server computer to deliver content. The server computer delivers the requested content to the user. During content delivery, the server computer causes the above-described living-body measurement system 100 to obtain blood flow information of the user who is viewing the content and to estimate an emotion. The server computer collects data regarding the estimated emotion for each piece of content and accumulates data indicating an association between the content and the emotion. Thus, the server computer can associate and record individual pieces of content and emotions elicited by the content for the user.

Figure 9:
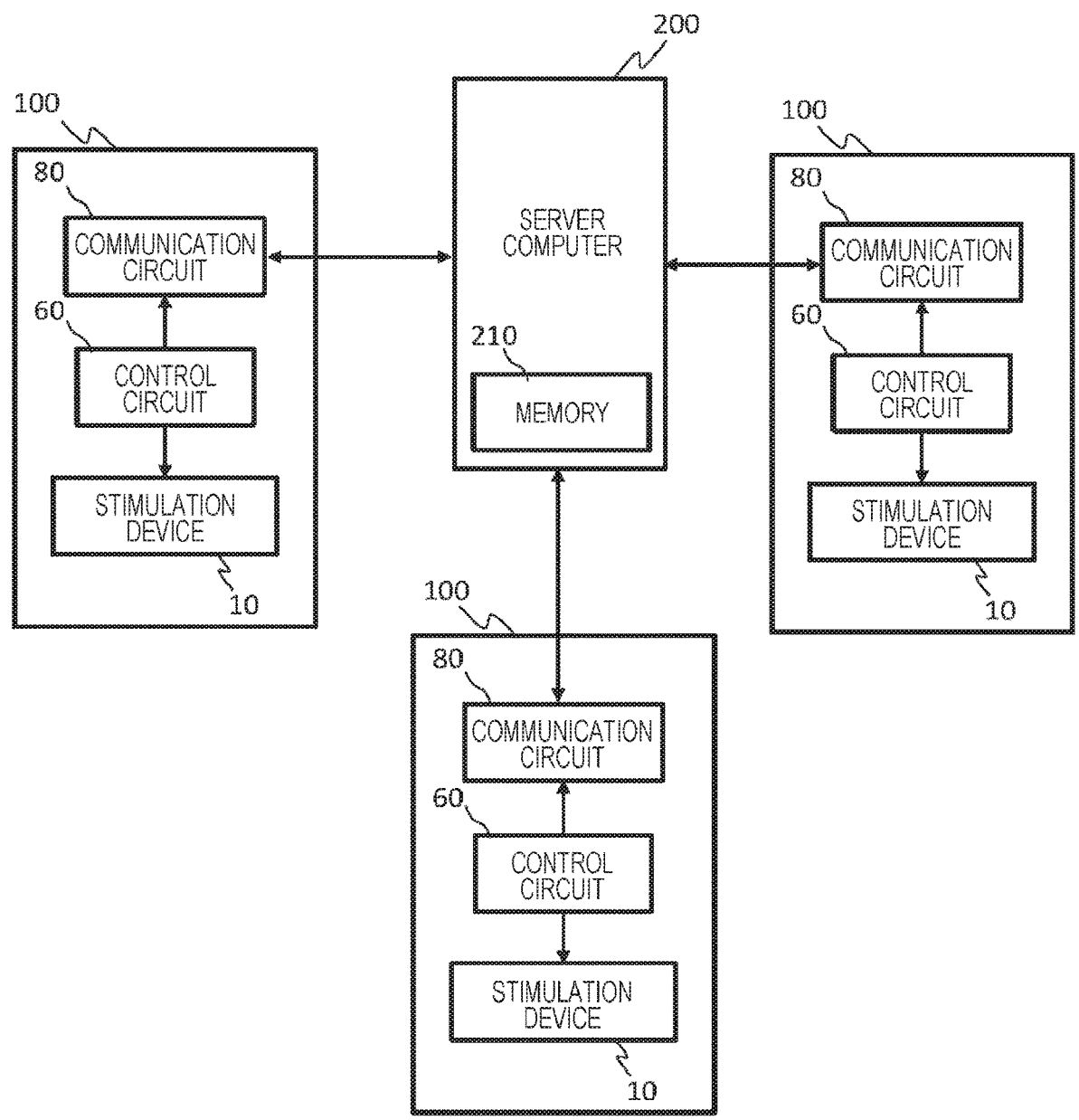
FIG. 9 is a diagram schematically illustrating a configuration example of a plurality of living-body measurement systems and a server computer.

FIG. 9 is a diagram schematically illustrating a configuration example of such a system. This system includes a plurality of living-body measurement systems 100 and a server computer 200. The server computer 200 is connected to the plurality of living-body measurement systems 100 through a network. Although three living-body measurement systems 100 are illustrated in FIG. 9, a larger number of living-body measurement systems 100 can be connected to the server computer 200.

Each living-body measurement system 100 includes a communication circuit 80, in addition to the constituent elements illustrated in FIG. 1A. Of the constituent elements of each living-body measurement system 100, only the stimulation device 10, the control circuit 60, and the communication circuit 80 are illustrated in FIG. 9.

The control circuit 60 in each of the living-body measurement systems 100 transmits data indicating an association between a stimulus and the emotion of a user to the server computer 200 via the communication circuit 80. For example, the control circuit 60 transmits data in which content viewed by a user and the emotion of the user who is viewing.

The server computer 200 collects data indicating the associations for a plurality of users and records the data to a memory 210. The server computer 200 associates, for example, user identifiers (IDs), content IDs, and emotion IDs with each other and records the IDs to a database. Based on the data collected from a large number of users, the server computer 200 can determine a stimulus (in this example, content) that elicits a specific emotion for the user. For example, with respect to each piece of content, the server computer 200 aggregates emotions felt by users who viewed the content in the past. The server computer 200 adds an identifier indicating an emotion felt by the largest number of users to the data of each piece of the content and records the data. The association between pieces of content and emotions can be updated upon accumulation of new information.

When a user requests viewing one piece of content, the server computer 200 transmits data of the content to the living-body measurement system 100. At this point in time, the server computer 200 selects, from pieces of content, another one or more pieces of content that elicits an emotion that is similar to the emotion associated with the transmitted content and notifies the control circuit 60 about information thereof.

In accordance with an instruction from the server computer 200, the control circuit 60 causes the stimulation device 10 to provide the selected one or more pieces of content. For example, content that can elicit an emotion of excitement or astonishment can be provided to the user.

7. Other Embodiments

In the example illustrated in FIG. 9, the stimulus can be content regarding an amusement, such as a movie, a game, or music. The stimulus may be another stimulus. The technology disclosed herein may be applied to, for example, controlling a device that gives a stimulus using at least one of light, vibration, heat, and odor or that stimulates at least one of other human five senses. The technology disclosed herein may also be applied to a system that controls a lighting device. In one embodiment, the lighting device has a function for adjusting illuminance or a color temperature. Each time illuminance or a color temperature is set, a control circuit in the system estimates the emotion of a user and accumulates data indicating an association between the illuminance and color temperature and the emotion. Based on the accumulated data, illuminance and a color temperature at which the user feels most comfortable may be determined, and the illuminance and the color temperature may be automatically set.

Figure 10:
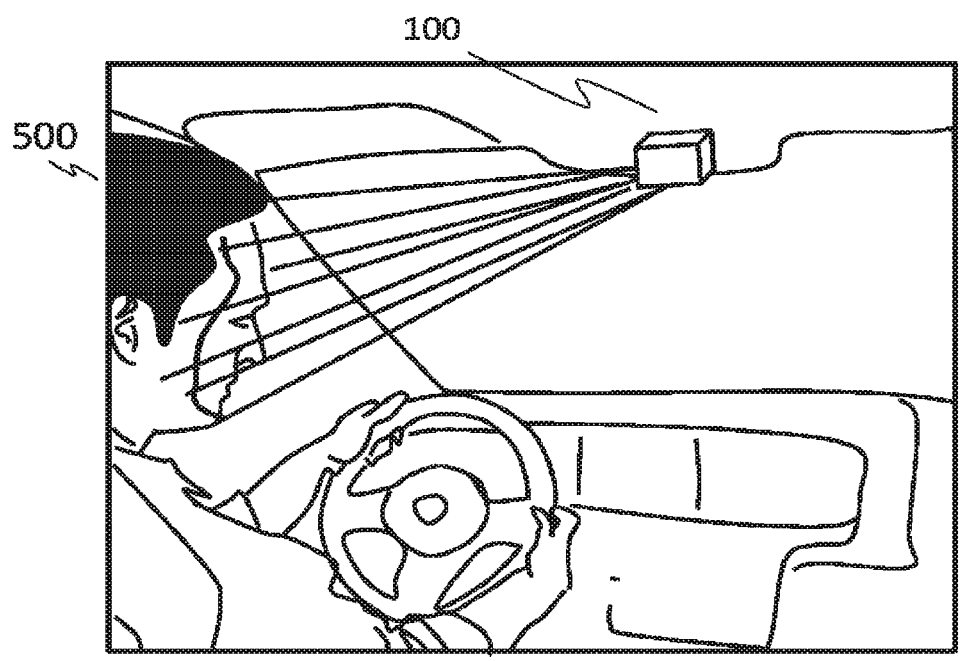
FIG. 10 is a view illustrating an application example in a vehicle.

FIG. 10 is a view illustrating a state in which the living-body measurement system 100 detects a psychological state of a vehicle driver who is a target person 500. The living-body measurement system 100 measures a surface blood flow state of the driver, based on the surface reflection components I1, and measures changes in the cerebral blood flow of the driver, based on the internal scattering components I2. Based on obtained data of the surface blood flow and data of the cerebral blood flow, a determination is made as to whether the driver is in a state in which he or she can drive, whether the driver is in a state in which he or she needs driving assistance, or the like. In the cerebral blood flow measurement, a database of cerebral blood flow rates or cerebral blood flow distributions of the driver during normal operations or a database of cerebral blood flow rates or cerebral blood flow distributions of the driver which are accumulated day-to-day is compared with the measurement data to determine a brain activity state of the driver. An affective psychological state, such as tension or anxiety, of the driver is determined from the surface blood flow measurement. When it is determined from the cerebral blood flow measurement data and the surface blood flow measurement data that it is dangerous to let the driver to drive, a message to that effect is output using sound, a message to that effect is displayed on a display, an announcement is made or music is played for making the driver relaxed, or an effect of a driving assist function equipped in the vehicle is increased. When the driver is driving, measures for making him or her pull over the vehicle may be taken.

Figure 11:
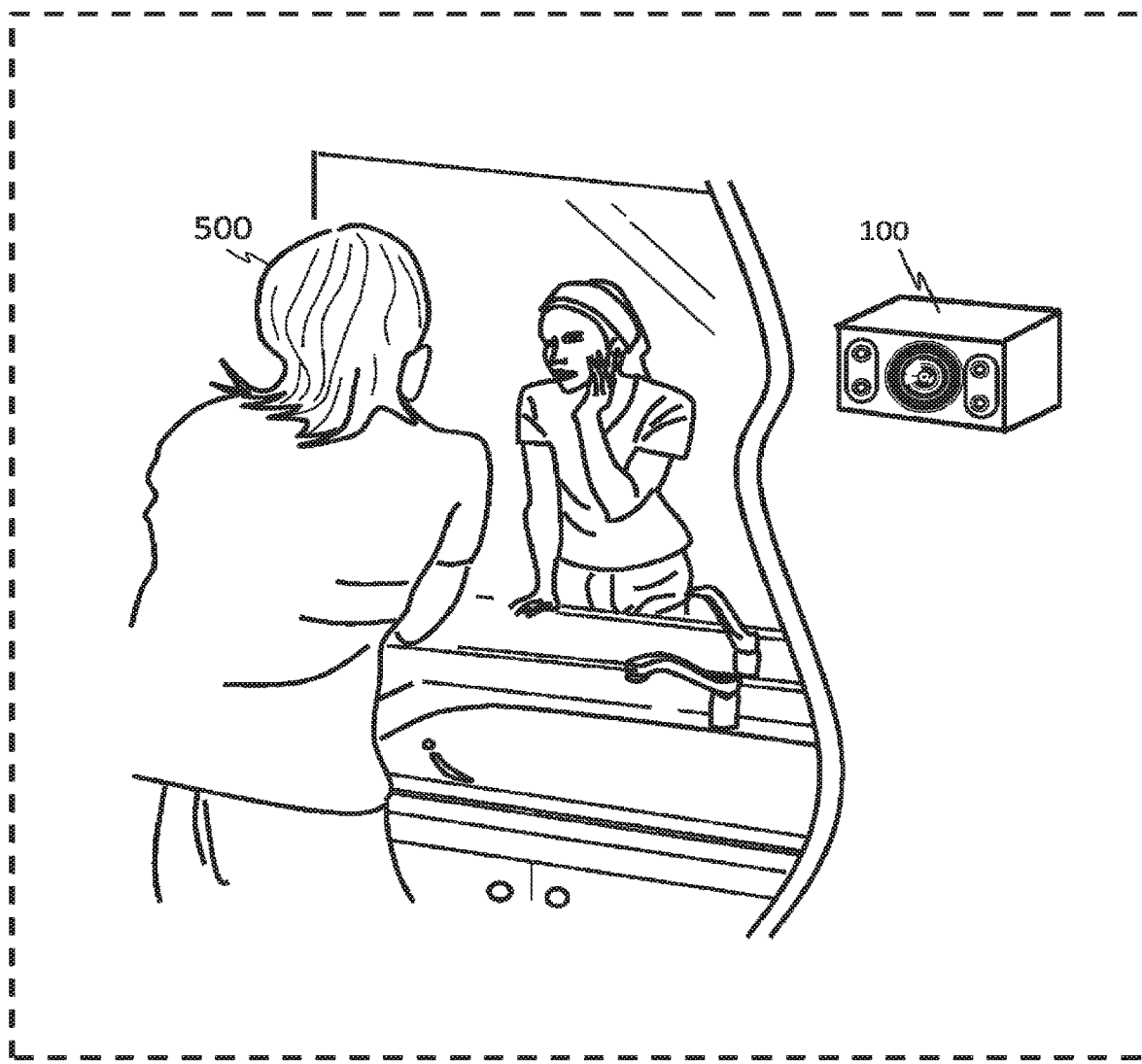
FIG. 11 is a view illustrating an application example in mental health checking.

FIG. 11 illustrates an example in which the living-body measurement system 100 is installed in a home or an office and is thereby used for mental health checking at home or in the office. Since the living-body measurement system 100 can obtain the living-body information and the brain activity information in a contactless manner, it can be installed, for example, at the back of a mirror at a washstand. Interference film coating is applied to the mirror so as to reflect visible light and transmit near-infrared (for example, light with a wavelength of 700 nm or more). Since the coating of an interference film, which reflects visible light, is applied, the mirror reflects the figure of a user who is a target person 500, but the camera installed at the back of the mirror is not visible to the user. Meanwhile, since the mirror transmits near-infrared, measurement light can be radiated to the user through the mirror. This, therefore, does not make the user aware of the presence of the camera, and thus the living-body information and the cerebral blood flow can be measured when the user is under a natural mental state. Also, the measurement can be performed from a position immediately in front of the user, and the forehead portion can be measured efficiently. In addition, during face washing, since the front hair is often secured with a hair band or the like, it is not necessary to instruct the user to raise the front hair, which serves as a shield, and thus the user is not bothered. Also, at the washstand, since the user stands in front of the mirror, measurement can be performed at a constant and near distance, which is an environment in which the stability of measurement increases.

A human detecting sensor, such as a pyroelectric sensor, may be installed in the vicinity of the living-body measurement system 100. Upon sensing a human, the human detecting sensor transmits a signal to the living-body measurement system 100, and the living-body measurement system 100 starts measurement on the human. Cooperating with the human detecting sensor allows driving of the light source and electrical circuitry in the living-body measurement system 100 to be stopped when no one is present, thus making it possible to reduce the power consumption.

Affect information, such as a tension state and an anxiety state of the user, can be obtained from changes in the surface blood flow measured by the living-body measurement system 100. Also, mental health condition data, such as the state of concentration, the degree of clear-headedness, or depression of mood, can be detected based on the cerebral blood flow information simultaneously obtained upon detecting the rear-end portion of the pulsed light. Since part of the surface blood flow information, in addition to the cerebral blood flow information, is superimposed on signals obtained from the rear end of the pulsed light, detecting the surface reflection components I1 separately makes it possible to eliminate components that provide noise, such as the tension state and the anxiety state of the user, and makes it possible to perform more accurate mental health checking.

Each time the user stands in front of the mirror, measurement using the living-body measurement system 100 may be performed, and data that is obtained may be accumulated. An abnormal change in a mental state in one day relative to an everyday normal state of the user can be detected from relative change information obtained through comparison of day-to-day data that are accumulated. Also, everyday measurement of time-series data is continually performed, and temporal moving average processing is performed on these pieces of time-series data, to thereby make it possible to eliminate high-frequency components representing temporary, irregular mental changes and make it possible to monitor low-frequency components representing changes in a long-term mental state for some years.

When the system detects changes in the physical condition, an estimated mental health state of the user is displayed on a display installed at the washstand or a display provided on a reflection mirror. Also, outputting day-to-day measurement results as a graph makes it possible to visualize the degree of health improvement and makes it possible to enhance the user's motivation for addressing improvement in healthcare. As another data display method, the measurement data may be transmitted to a smartphone or tablet terminal of the user via Wi-Fi (registered trademark), Wi-Fi Direct (registered trademark), Bluetooth (registered trademark), a cloud, or the like and be displayed on the smartphone or the tablet terminal. Also, the living-body measurement system 100 may be installed at a hospital, a school, a healthcare room, or the like, other than in a home or an office.

Next, a description will be given of a specific example of the stimulation device 10, the output device 40, and the input device 50.

Figure 12:
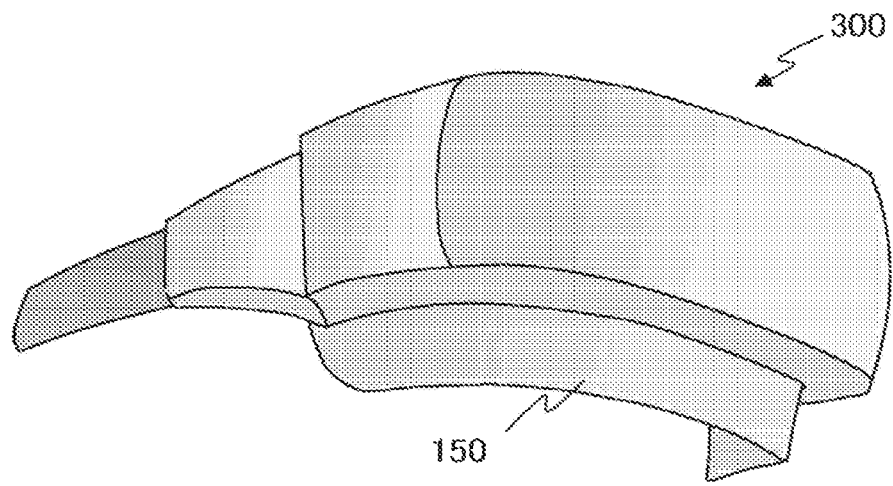
FIG. 12 is a view schematically illustrating a head-mounted device.

FIG. 12 is a view schematically illustrating a head-mounted device 300. The head-mounted device 300 includes a display 150. The display 150 in this example functions as a stimulation device and an output device. The display 150 displays video of content or an image for a task or the like. The display 150 also displays an image indicating an estimation result of the emotion of a user. For example, the display 150 can display the result of the classification of the emotion group determined in step S313 illustrated in FIG. 7. As described above, the head-mounted device 300 has functions of both a stimulation device and an output device. In this example, an input device can be an operation button provided on the head-mounted device 300, a touch screen, or a sound input device. The surface blood flow state of the user is measured based on the surface reflection components I1, and changes in the cerebral blood flow of the user are measured based on the internal scattering components I2. Affect information of the user, such as tension, anxiety, pleasure, or excitement, can be detected from the surface blood flow state. Also, reason information, such as cognition, working memory, or the state of concentration, of the user can be detected from the cerebral blood flow information. Combining these pieces of affect information and reason information of the user makes it possible to estimate a more complex psychological state of the user. Based on a result of determination, video of content, sound, a story, or the like may be changed as appropriate in accordance with the psychological state of the user.

Figure 13:
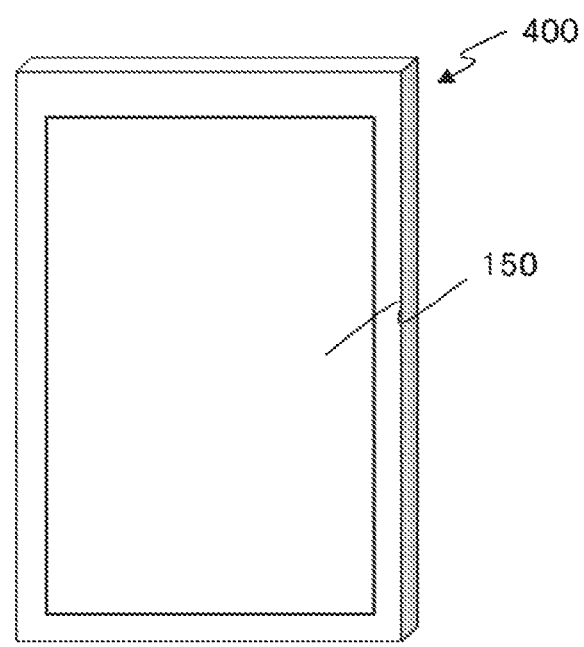
FIG. 13 is a view schematically illustrating a smartphone.

FIG. 13 is a view schematically illustrating a smartphone 400. The smartphone 400 has a display 150. The display 150 serves as the stimulation device 10 to present video. A speaker built into the smartphone 400 provides sound as a stimulus. The display 150 also functions as the output device 40. For example, the display 150 displays a result of the emotion group classification in step S313 illustrated in FIG. 7. The display 150 has a touch screen and also functions as the input device 50. Accordingly, the smartphone 400 has functions of the stimulation device 10, the output device 40, and the input device 50.

The present disclosure also includes a method for the operations executed by the control circuit 60 and a computer program that specifies the operations executed by the control circuit 60. Such a computer program is stored in a recording medium and causes the control circuit 60 to execute the above-described operations.

The present disclosure includes a system, a computer program, a computer-readable non-transitory recording medium, and a method described below.

The system according to one aspect of the present disclosure includes: a light source that emits pulsed light with which a head portion of a user is illuminated; a photodetector that detects at least part of reflection pulsed light that returns from the head portion and that outputs one or more signals corresponding to an intensity of the at least part of the reflection pulsed light; electrical circuitry that controls the light source and the photodetector to process the one or more signals output from the photodetector; and a first memory that stores an emotion model indicating a relationship between the one or more signals and emotions. Based on a change in the one or more signals, the electrical circuitry selects at least one emotion from among the emotions by referring to the emotion model. The one or more signals include a first signal corresponding to an intensity of first part of the reflection pulsed light and a second signal corresponding to an intensity of second part of the reflection pulsed light, the second part being different from the first part. The first part incudes part before a falling period is started, the falling period being a period from start to end of a decrease of an intensity of the reflection pulsed light; and the second part includes at least part in the falling period.

In this system, the head portion of the user is illuminated with pulsed light, and reflection pulsed light thereof is detected. At least one emotion is selected from the emotion model including a plurality of pre-defined emotions, based on a change in one or more signals corresponding to the intensity of the detected light. This makes it possible to more accurately estimate the emotion of the user. In this system, the one or more signals include first and second signals. The first signal includes information on facial blood flow of the user. The second signal includes information on cerebral blood flow of the user.

In the system according to one aspect of the present disclosure, the system may further include a stimulation device that provides at least one stimulus to the user; the electrical circuitry may cause the stimulation device to provide the at least one stimulus; and the at least one emotion may be selected by referring to the emotion model, based on a change in the one or more signals generated in response to the at least one stimulus.

In this system, the head portion of the user is illuminated with pulsed light when a stimulus is provided to the user, and the reflection pulsed light is detected. At least one emotion is selected from the emotion model including a plurality of pre-defined emotions, based on a change in one or more signals corresponding to the intensity of the detected light. This makes it possible to more accurately estimate the emotion of the user.

In the system according to one aspect of the present disclosure, the emotion model may include emotion groups; in the emotion model, each of the emotions may be classified into any of the emotion groups; and the electrical circuitry may select at least one emotion group from among the emotion groups by referring to the emotion model, based on a combination of a first value indicating a difference between the first signal when the at least one stimulus is provided to the user and the first signal when the at least one stimulus is not provided to the user and a second value indicating a difference between the second signal when the at least one stimulus is provided to the user and the second signal when the at least one stimulus is not provided to the user.

In this system, at least one emotion group can be determined from the emotion model, based on a combination of a first value indicating the amount of change in the facial blood flow of the user between a rest time and a stimulation time and a second value indicating the amount of change in the cerebral blood flow of the user between the rest time and the stimulation time.

In the system according to one aspect of the present disclosure, the emotion model may include first to fourth emotion groups; in the emotion model, each of the emotions may be classified into any of the first to fourth emotion groups; and the electrical circuitry may select the first emotion group, when the first value is larger than a first threshold, and the second value is larger than a second threshold, select the second emotion group, when the first value is smaller than or equal to the first threshold, and the second value is larger than the second threshold, select the third emotion group, when the first value is smaller than or equal to the first threshold, and the second value is smaller than or equal to the second threshold, and select the fourth emotion group, when the first value is larger than the first threshold, and the second value is smaller than or equal to the second threshold.

In this system, the emotion model includes first to fourth emotion groups. The emotion of the user is classified into any of the first to fourth emotion groups, in accordance with a magnitude relationship between the first value and the first threshold and a magnitude relationship between the second value and the second threshold.

In the system according to one aspect of the present disclosure, the electrical circuitry may cause an output device to output at least one selected from the group consisting of an image and sound that query the user as to whether the at least one emotion corresponds to an actual emotion of the user; and the output device may include at least one selected from the group consisting of a display and a speaker.

In this system, the output device can query the user as to whether the selected at least one emotion corresponds to an actual emotion of the user.

The system according to one aspect of the present disclosure may further include: an input device that receives an input of the user. When the user uses the input device to perform input indicating that the at least one emotion corresponds to the actual emotion of the user, the electrical circuitry may record, to a second memory, data indicating an association between the at least one stimulus and the at least one emotion.

In this system, the user uses the input device to make a response indicating that the at least one emotion corresponds to an actual emotion of the user. This makes it possible to record the data indicating the association between the stimulus and at least one emotion to the second memory.

In the system according to one aspect of the present disclosure, the stimulation device may be capable of providing, to the user, the at least one stimulus selected from a plurality of stimuli; the electrical circuitry may be connected to a server computer through a network, the server computer including the second memory; the server computer may notify the electrical circuitry so as to select the at least one stimulus based on the data; and based on the notification from the server computer, the electrical circuitry may cause the stimulation device to provide, to the user, the at least one stimulus selected from the plurality of stimuli.

In this system, an external server computer collects data indicating an association between stimuli and at least one emotion, the data being recorded for a plurality of users. Based on the collected data, the external server computer issues an instruction to the system through a network. Based on the instruction, a stimulus is provided to each user. This makes it possible to elicit a specific emotion for each user.

In the system according to one aspect of the present disclosure, the at least one stimulus may include at least one selected from the group consisting of video and sound.

In the system according to one aspect of the present disclosure, the electrical circuitry may select the at least one emotion from among the emotions, based on a change in the first signal and a change in the second signal.

Also, a program according to one aspect of the present disclosure is a program that is used in a system and that is executed by a computer. The system includes: a light source that emits pulsed light with which a head portion of a user is illuminated; and a photodetector that detects at least part of reflection pulsed light that returns from the head portion and that outputs one or more signals corresponding to an intensity of the at least part of the reflection pulsed light. The program includes: causing the light source to emit the pulsed light; causing the photodetector to detect the reflection pulsed light and to output the one or more signals; and selecting at least one emotion from among emotions by referring to an emotion model indicating a relationship between the one or more signals and the emotions, based on a change in the one or more signals. The one or more signals include a first signal corresponding to an intensity of first part of the reflection pulsed light and a second signal corresponding to an intensity of second part of the reflection pulsed light, the second part being different from the first part. The first part incudes part before a falling period is started, the falling period being a period from start to end of a decrease of an intensity of the reflection pulsed light; and the second part includes at least part in the falling period.

In the program according to one aspect of the present disclosure, the system may further include a stimulation device that provides at least one stimulus to the user. The program according to one aspect of the present disclosure may further include causing the stimulation device to provide the at least one stimulus; and in the selecting, the at least one emotion may be selected by referring to the emotion model, based on a change in the one or more signals generated in response to the at least one stimulus.

In the program according to one aspect of the present disclosure, the emotion model may include emotion groups, and in the emotion model, each of the emotions may be classified into any of the emotion groups. The program according to one aspect of the present disclosure may further include selecting at least one emotion group from the emotion groups by referring to the emotion model, based on a combination of a first value indicating a difference between the first signal when the at least one stimulus is provided to the user and the first signal when the at least one stimulus is not provided to the user and a second value indicating a difference between the second signal when the at least one stimulus is provided to the user and the second signal when the at least one stimulus is not provided to the user.

In the program according to one aspect of the present disclosure, the emotion model may include first to fourth emotion groups, and in the emotion model, each of the emotions may be classified into any of the first to fourth emotion groups. The program according to one aspect of the present disclosure may further include: selecting the first emotion group, when the first value is larger than a first threshold, and the second value is larger than a second threshold; selecting the second emotion group, when the first value is smaller than or equal to the first threshold, and the second value is larger than the second threshold; selecting the third emotion group, when the first value is smaller than or equal to the first threshold, and the second value is smaller than or equal to the second threshold; and selecting the fourth emotion group, when the first value is larger than the first threshold, and the second value is smaller than or equal to the second threshold.

The program according to one aspect of the present disclosure may further include causing an output device to output at least one selected from the group consisting of an image and sound that query the user as to whether the at least one emotion corresponds to an actual emotion of the user is further executed; and the output device may include at least one selected from the group consisting of a display and a speaker.

In the program according to one aspect of the present disclosure, the system may further include an input device that receives an input of the user. The program according to one aspect of the present disclosure may further include recording, to a memory, data indicating an association between the at least one stimulus and the at least one emotion is further executed when the user uses the input device to perform input indicating that the at least one emotion corresponds to the actual emotion of the user.

Also, a computer-readable non-transitory recording medium according to one aspect of the present disclosure is a computer-readable non-transitory recording medium storing a program used in a system including: a light source that emits pulsed light with which a head portion of a user is illuminated; and a photodetector that detects at least part of reflection pulsed light that returns from the head portion and that outputs one or more signals corresponding to an intensity of the at least part of the reflection pulsed light. When the program is executed by the computer, causing the light source to emit the pulsed light, causing the photodetector to detect the reflection pulsed light and to output the one or more signals, and selecting at least one emotion from among emotions by referring to an emotion model indicating a relationship between the one or more signals and the emotions, based on a change in the one or more signals are executed. The one or more signals include a first signal corresponding to an intensity of first part of the reflection pulsed light and a second signal corresponding to an intensity of second part of the reflection pulsed light, the second part being different from the first part. The first part incudes part before a falling period is started, the falling period being a period from start to end of a decrease of an intensity of the reflection pulsed light; and the second part includes at least part in the falling period.

In the computer-readable non-transitory recording medium according to one aspect of the present disclosure, the system may further include a stimulation device that provides at least one stimulus to the user. In the computer-readable non-transitory recording medium according to one aspect of the present disclosure, when the program is executed by the computer, causing the stimulation device to provide the at least one stimulus may be further executed; and in the selecting, the at least one emotion may be selected by referring to the emotion model, based on a change in the one or more signals generated in response to the at least one stimulus.

In the computer-readable non-transitory recording medium according to one aspect of the present disclosure, the emotion model may include emotion groups, and in the emotion model, each of the emotions may be classified into any of the emotion groups. In the computer-readable non-transitory recording medium according to one aspect of the present disclosure, when the program is executed by the computer, selecting at least one emotion group from among the emotion groups may be further executed by referring to the emotion model, based on a combination of a first value indicating a difference between the first signal when the at least one stimulus is provided to the user and the first signal when the at least one stimulus is not provided to the user and a second value indicating a difference between the second signal when the at least one stimulus is provided to the user and the second signal when the at least one stimulus is not provided to the user.

The computer-readable non-transitory recording medium according to one aspect of the present disclosure, the emotion model may include first to fourth emotion groups, and in the emotion model, each of the emotions may be classified into any of the first to fourth emotion groups. In the computer-readable non-transitory recording medium according to one aspect of the present disclosure, when the program is executed by the computer, selecting the first emotion group, when the first value is larger than a first threshold, and the second value is larger than a second threshold, selecting the second emotion group, when the first value is smaller than or equal to the first threshold, and the second value is larger than the second threshold, selecting the third emotion group, when the first value is smaller than or equal to the first threshold, and the second value is smaller than or equal to the second threshold, and selecting the fourth emotion group, when the first value is larger than the first threshold, and the second value is smaller than or equal to the second threshold may be further executed.

In the computer-readable non-transitory recording medium according to one aspect of the present disclosure, when the program is executed by the computer, causing an output device to output at least one selected from the group consisting of an image and sound that query the user as to whether the at least one emotion corresponds to an actual emotion of the user may be further executed. The output device may include at least one selected from the group consisting of a display and a speaker.

In the computer-readable non-transitory recording medium according to one aspect of the present disclosure, the system may further include an input device that receives an input of the user. In the computer-readable non-transitory recording medium according to the present disclosure, when the program is executed by the computer, recording, to a memory, data indicating an association between the at least one stimulus and the at least one emotion may be further executed when the user uses the input device to perform input indicating that the at least one emotion corresponds to the actual emotion of the user.

In the computer-readable non-transitory recording medium according to the present disclosure, the selecting of the at least one emotion from among the emotions based on the change in the one or more signals may be selecting the at least one emotion from among the emotions based on a change in the first signal and a change in the second signal.

Also, a method according to one aspect of the present disclosure is a method used in a system including: a light source that emits pulsed light with which a head portion of a user is illuminated; and a photodetector that detects at least part of reflection pulsed light that returns from the head portion and that outputs one or more signals corresponding to an intensity of the at least part of the reflection pulsed light. The method includes: causing the light source to emit the pulsed light; causing the photodetector to detect the reflection pulsed light and to output the one or more signals; and selecting at least one emotion from among emotions by referring to an emotion model indicating a relationship between the one or more signals and the emotions, based on a change in the one or more signals. The one or more signals include a first signal corresponding to an intensity of first part of the reflection pulsed light and a second signal corresponding to an intensity of second part of the reflection pulsed light, the second part being different from the first part. The first part incudes part before a falling period is started, the falling period being a period from start to end of a decrease of an intensity of the reflection pulsed light; and the second part includes at least part in the falling period.

In the method according to one aspect of the present disclosure, the system may further include a stimulation device that provides at least one stimulus to the user. The method according to one aspect of the present disclosure may further include causing the stimulation device to provide the at least one stimulus; and in the selecting, the at least one emotion may be selected by referring to the emotion model, based on a change in the one or more signals generated in response to the at least one stimulus.

In the method according to one aspect of the present disclosure, the emotion model may include emotion groups, and in the emotion model, each of the emotions may be classified into any of the emotion groups. The method according to one aspect of the present disclosure may further include selecting at least one emotion group from the emotion groups by referring to the emotion model, based on a combination of a first value indicating a difference between the first signal when the at least one stimulus is provided to the user and the first signal when the at least one stimulus is not provided to the user and a second value indicating a difference between the second signal when the at least one stimulus is provided to the user and the second signal when the at least one stimulus is not provided to the user.

In the method according to one aspect of the present disclosure, the emotion model may include first to fourth emotion groups, and in the emotion model, each of the emotions may be classified into any of the first to fourth emotion groups. The method according to one aspect of the present disclosure may further include: selecting the first emotion group, when the first value is larger than a first threshold, and the second value is larger than a second threshold; selecting the second emotion group, when the first value is smaller than or equal to the first threshold, and the second value is larger than the second threshold; selecting the third emotion group, when the first value is smaller than or equal to the first threshold, and the second value is smaller than or equal to the second threshold; and selecting the fourth emotion group, when the first value is larger than the first threshold, and the second value is smaller than or equal to the second threshold.

The method according to one aspect of the present disclosure may further include causing an output device to output at least one selected from the group consisting of an image and sound that query the user as to whether the at least one emotion corresponds to an actual emotion of the user. The output device may include at least one selected from the group consisting of a display and a speaker.

In the method according to one aspect of the present disclosure, the system may further include an input device that receives an input of the user. The method according to one aspect of the present disclosure may further include recording, to a memory, data indicating an association between the at least one stimulus and the at least one emotion when the user uses the input device to perform input indicating that the at least one emotion corresponds to the actual emotion of the user.

In the method according to one aspect of the present disclosure, the selecting of the at least one emotion from among the emotions based on the change in the one or more signals may be selecting the at least one emotion from among the emotions based on a change in the first signal and a change in the second signal.

Also, a system according to another aspect of the present disclosure includes: a light source that emits pulsed light with which a head portion of a user is illuminated; a photodetector that detects at least part of reflection pulsed light that returns from the head portion and that outputs one or more signals corresponding to an intensity of the at least part of the reflection pulsed light; and electrical circuitry that controls the light source and the photodetector to process the one or more signals output from the photodetector. The electrical circuitry causes the light source to emit the pulsed light, causes the photodetector to detect and output, as a brain activity signal, internal scattering components included in the reflection pulsed light and diffused in a brain of the user, causes the photodetector to detect and output, as a facial blood flow signal, surface reflection components included in the reflection pulsed light and reflected by a surface of skin of the user, and generates and outputs a signal indicating a psychological state of the user, based on the facial blood flow signal and the brain activity signal.

In the system according to the other aspect of the present disclosure, electrical circuitry, the electrical circuitry may cause the photodetector to detect first part of the reflection pulsed light to detect the surface reflection components and to detect second part of the reflection pulsed light to detect the internal scattering components, the second part being different from the first part. The first part may include part before a falling period is started, the falling period being a period from start to end of a decrease of an intensity of the reflection pulsed light; and the second part may include at least part in the falling period.

What is claimed is:

1. A system comprising:
a light source;
a photodetector; and
electrical circuitry,
wherein the electrical circuitry
causes the light source to emit at least one pulsed light with which a user is illuminated,
causes the photodetector to detect internal scattering components included in at least one reflection pulsed light that returns from the user, the internal scattering components being diffused in a brain of the user,
causes the photodetector to detect surface reflection components included in the at least one reflection pulsed light, the surface reflection components being reflected by a surface of the user,
generates a first signal indicating an amount of change in brain blood flow of the user based on the internal scattering components, and
generates a second signal indicating an amount of change in facial blood flow of the user based on the surface reflection components.

2. The system according to claim 1, wherein
the electrical circuitry
determines a psychological state of the user based on the first signal and the second signal.

3. The system according to claim 1, wherein the facial blood flow corresponds to scalp blood flow.

4. The system according to claim 2, wherein the psychological state indicates at least one selected from the group consisting of a mood, an emotion, a health condition, a thermal sensation, and a degree of concentration.

5. The system according to claim 1, wherein
the at least one reflection pulsed light includes a first reflection pulsed light and a second reflection pulsed, and
the electrical circuitry
causes the photodetector to detect the internal scattering components included in the first reflection pulsed light, and
causes the photodetector to detect the surface reflection components included in the second reflection pulsed light.

6. A system comprising:
a light source;
a photodetector; and
electrical circuitry,
wherein the electrical circuitry:
causes the light source to emit at least one pulsed light with which a user is illuminated,
causes the photodetector to detect internal scattering components included in at least one reflection pulsed light that returns from the user, the internal scattering components being diffused in a brain of the user,
causes the photodetector to detect surface reflection components included in the at least one reflection pulsed light, the surface reflection components being reflected by a surface of the user,
determines a psychological state of the user, based on the internal scattering components and the surface reflection components,
causes the photodetector to detect first part of the at least one reflection pulsed light to detect the surface reflection components, and
causes the photodetector to detect second part of the at least one reflection pulsed light to detect the internal scattering components,
the first part includes part before a falling period is started, the falling period being a period from start to end of a decrease of an intensity of the at least one reflection pulsed light, and
the second part includes at least part in the falling period.

7. The system according to claim 2, wherein
the user is a vehicle driver who drives a vehicle equipped with a driving assist function,
the electrical circuitry determines whether or not it is dangerous to let the user to drive based on the psychological state of the user, and
when the electrical circuitry determines that it is dangerous to let the user to drive, the electrical circuitry outputs a control signal that increases an effect of the driving assist function.

8. A method used in a system comprising:
a light source; and
a photodetector; and
electrical circuitry, the method including:
causing the light source to emit at least one pulsed light with which a user is illuminated;

causing the photodetector to detect internal scattering components included in at least one reflection pulsed light that returns from the user, the internal scattering components being diffused in a brain of the user;

causing the photodetector to detect surface reflection components included in the at least one reflection pulsed light, the surface reflection components being reflected by a surface of the user;

generating a first signal indicating an amount of change in brain blood flow of the user based on the internal scattering components; and generating a second signal indicating an amount of change in facial blood flow of the user based on the surface reflection components.

9. The method of claim 8, further comprising determining a psychological state of the user based on the first signal and the second signal.

\* \* \* \* \*